(12) United States Patent
Mertens et al.

(10) Patent No.: US 8,389,209 B2
(45) Date of Patent: Mar. 5, 2013

(54) TEST DEVICE FOR RAPID DIAGNOSTICS

(75) Inventors: Pascal Mertens, Seilles (BE); Laurence Denorme, Isnes (BE); Thierry Leclipteux, Wepion (BE)

(73) Assignee: Coris Bioconcept, Gembloux (BE)

( * ) Notice: Subject to any disclaimer, the term of this patent is extended or adjusted under 35 U.S.C. 154(b) by 756 days.

(21) Appl. No.: 12/096,008

(22) PCT Filed: Dec. 8, 2006

(86) PCT No.: PCT/EP2006/011791
§ 371 (c)(1),
(2), (4) Date: Jun. 3, 2008

(87) PCT Pub. No.: WO2007/065695
PCT Pub. Date: Jun. 14, 2007

(65) Prior Publication Data
US 2009/0162833 A1 Jun. 25, 2009

(30) Foreign Application Priority Data
Dec. 8, 2005 (WO) .................. PCT/EP2005/013159

(51) Int. Cl.
*C12Q 1/70* (2006.01)
*G01N 33/53* (2006.01)

(52) U.S. Cl. .......................................................... 435/5

(58) Field of Classification Search ........................ None
See application file for complete search history.

(56) References Cited

U.S. PATENT DOCUMENTS

| | | | |
|---|---|---|---|
| 5,162,237 A * | 11/1992 | Messenger et al. | 436/523 |
| 7,285,426 B2 * | 10/2007 | Bohannon et al. | 436/514 |
| 2002/0001818 A1 | 1/2002 | Brock | |
| 2003/0096424 A1 | 5/2003 | Mao et al. | |
| 2004/0023412 A1 | 2/2004 | Carlsson et al. | |
| 2005/0227371 A1 | 10/2005 | Gokhan | |
| 2006/0205086 A1 * | 9/2006 | Hu | 436/514 |

FOREIGN PATENT DOCUMENTS
WO 98/32019 7/1998

OTHER PUBLICATIONS

International Search Report dated Mar. 16, 2007.

* cited by examiner

*Primary Examiner* — Benjamin P Blumel
(74) *Attorney, Agent, or Firm* — Knobbe, Martens, Olson & Bear LLP

(57) ABSTRACT

Devices for detecting analytes or analogues thereof in a biological sample are disclosed. The device includes a solid support. The solid support has several juxtaposed zones. The sample is able to migrate from a sample receiving zone towards a detection zone. The analyte, if present, is detected in the detection zone. Both zones have material allowing a capillary flow of the sample through the zones. In between the zones, there is an intermediate zone of transport of the sample which is free from any capillary material. This allows the ample to migrate by gravitational forces on the support laid in a vertical position. Methods for detecting analytes or analogues thereof in a biological sample using the device are also disclosed.

11 Claims, 8 Drawing Sheets

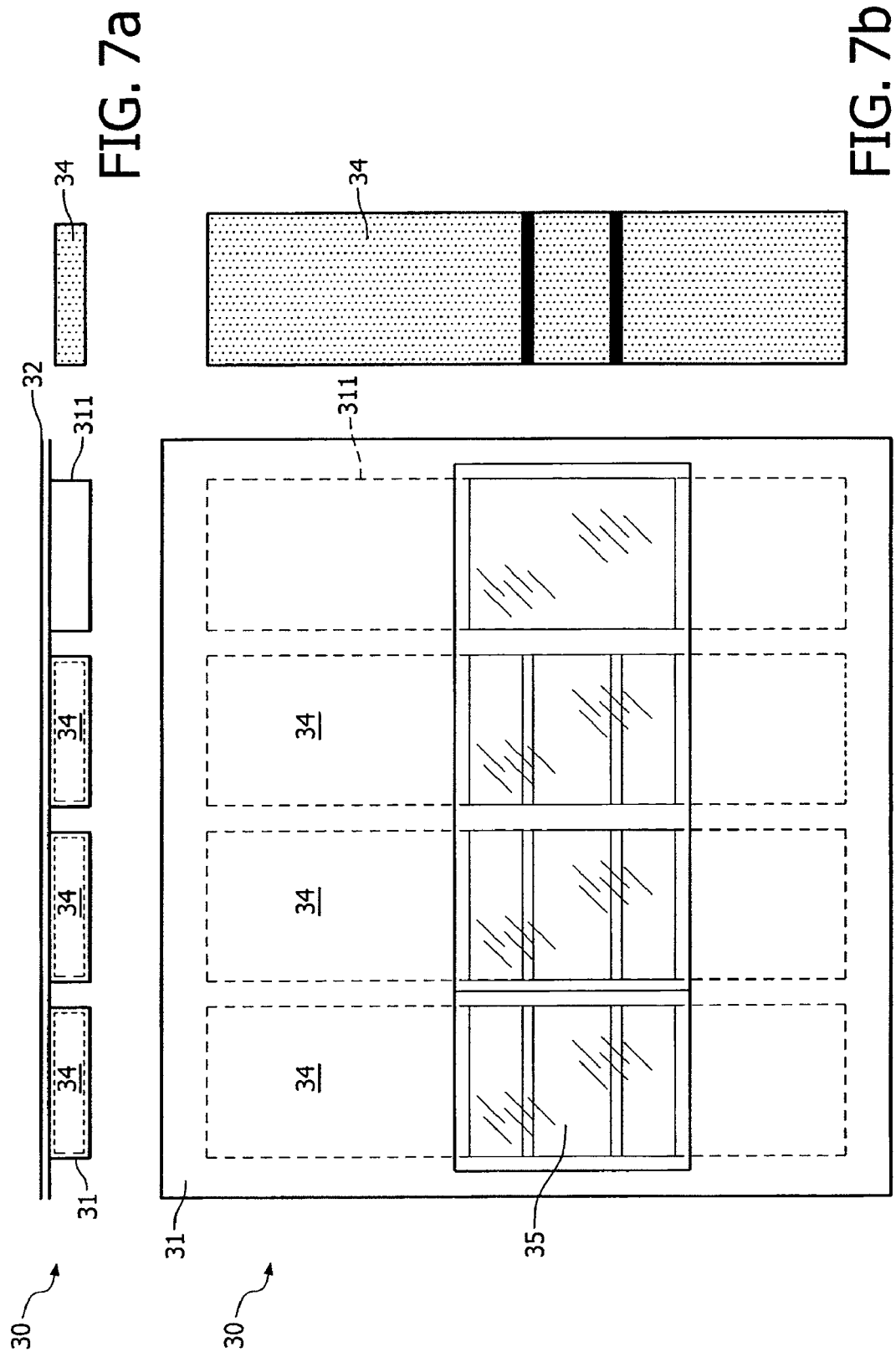

TEST DEVICE FOR RAPID DIAGNOSTICS

CROSS-REFERENCE TO RELATED APPLICATIONS

This application is the U.S. National Phase under 35 U.S.C. §371 of International Application PCT/EP2006/011791, filed Dec. 8, 2006, which claims priority to PCT/EP2005/013159, filed Dec. 8, 2005.

FIELD OF THE INVENTION

This invention relates to methods and devices for detecting analytes or analogues thereof in a biological sample. This invention relates to improved rapid tests such as "dipsticks" devices. The invention in particular relates to a test device made of one or more active sides, in order to allow mono or multiplex detections, quantitative or semi-quantitative detections. The devices described in this invention allow detecting or identifying various biologicals or chemicals with one manipulation.

BACKGROUND OF THE INVENTION

Several approaches have been developed for detection of analytes in a biological sample for routine diagnostics in diagnostic laboratories via for instance immunochromatography.

EP 0 088 636, EP 0 186 799, EP 0 284 232 and WO 88/08534 disclose sheet-like chromatographic devices comprising at least a first and a second zone or region. Prior art devices disclosed in these documents comprise:
- a first region or zone containing porous active material to allow liquid to move to the sensitized region coated with specific reagents. This first zone or region comprises a detection reagent dried on it or impregnated into it. It may further contain an application (sub)zone and/or an absorption (sub)zone. This first zone is generally referred to as the application zone;
- a second region or zone, also referred to as the detection zone, made of porous active material on which specific reagents are adsorbed. Some of these reagents laid down onto a subzone (e.g. a line) of the second region of the device are specific for the analyte to be detected and should react with the sample analyte-labeling reagent complex while other non-specific reagents eventually laid down onto a further subzone (e.g. as a further line) of the second region are dedicated to react with the excess of the detection reagent. This second zone or region, preferably made out of nitrocellulose, may also contain a control subzone, preferably behind the detection zone; and
- a third region or zone made of porous material dedicated to absorb excess of liquid coming through the first and second regions. This region is generally referred to as the absorbent or absorption region.

The (immuno)chromatographic devices of the prior art may have a plastic or other backing support and/or may be comprised in a water-impervious housing.

The three regions are in capillary contact to allow liquid movements from the application zone to the third region.

Although useful, currently available chromatographic devices using test strips have a number of drawbacks. Many samples, such as fecal samples, contain particulate matter that can clog the pores of the chromatographic medium, greatly hindering the immunochromatographic process. In addition it is frequently difficult with existing chromatographic test devices to apply the sample to the chromatographic medium so that the sample front moves uniformly through the chromatographic medium to ensure that the sample reaches the area where binding is to occur in a uniform, straight-line manner.

Sample preparation and waste generation are responsible for other problems with currently available devices and techniques for immunochromatography. It is rarely possible to apply a sample (such as feces) or a sampling device (such as a throat swab) directly to the chromatographic medium. Several extraction and pretreatment reactions are usually required before the sample can be applied to the chromatographic medium. These reactions are typically carried out by the physician or technician performing the test in several small vessels, such as test tubes or microfuge tubes, requiring the use of transfer devices such as pipettes. Each of these devices is then contaminated and must be disposed of using special precautions so that workers or people who may inadvertently come into contact with the waste do not become contaminated.

Therefore, it would be desirable to have a chromatographic assay device capable of receiving a possibly contaminated sample or a sample preparation device directly so as to eliminate the need for extraction vessels and transfer devices. Such a device, preferably in the form of a test strip, should also be capable of performing assays on samples containing particulates without clogging or without interference and should be able to deliver the sample to the chromatographic medium uniformly and evenly to improve accuracy and precision of the test. This aspect of an improved assay device is particularly important in avoiding false negatives and false positives.

AIMS OF THE INVENTION

The present invention aims to provide highly flexible sheet-like devices suitable for the detection of multiple analytes or analogues thereof in a solution or biological sample, these detections being carried out on the same device. The sheet-like device is designed to allow liquid movement by gravity and capillarity.

SUMMARY OF THE INVENTION

In a first aspect, the present invention provides a (gravity driven) test device made of one or more active sides, in order to allow mono or multiplex detections, quantitative or semi-quantitative detections, through a gravity driven process that will allow a liquid sample to come in contact with the different reactive zones of the device.

In particular, the present invention provides a test device for the detection of at least one analyte in a sample, comprising: a solid support, whereon is provided several juxtaposed zones, whereby the sample is able to migrate from a sample receiving zone towards a sample detection zone, whereby an at least one analyte if present is detected, whereby both zones comprises material allowing a capillary flow of the sample through said zones, characterized in that in between said zones an intermediate zone of transport of the sample is provided which is free from any capillary material, allowing the sample to migrate by gravitational forces on the support, when laid in a vertical position.

In a particular embodiment of the present invention, the present gravity driven test device is particularly suited for immunodetection, and comprises capture reagents that are immunoreagents.

In a second aspect, the present invention provides an analyte detection method, for the detection of at least one analyte in a sample, comprising the step of contacting a test device according to the present invention with a sample and allowing the sample to move from the top of the device to the bottom of the device, by gravity through a non-capillary zone, and detecting said at least one analyte.

In particular, the analyte detection method comprises contacting a sample receiving zone on the device with a sample, allowing the sample to migrate by capillarity through the sample receiving zone to a non capillary zone, allowing the sample to migrate through the non capillary zone by gravity to a detection zone and allowing the sample to migrate through the detection zone by capillarity and detecting the analyte.

In a particular embodiment, said test device (1) comprises on one or more sides of a solid support (18), arranged from one end of the device to the other end of the device:
- a first capillary zone comprising a sample application zone (2);
- a second capillary zone comprising a detection zone (4), optionally an intermediate zone (6), disposed next to said detection zone (4), and optionally an absorbent zone or region (5) disposed next to said detection zone (4), said detection zone (4) optionally comprising a control subzone; and
- a non-capillary zone (14) which separates the sample application zone (2) from the detection zone (4) or the optional intermediate zone (6), wherein the detection zone (4) comprises at least one capture reagents specifically recognizing the at least one analyte or analogue thereof; and
wherein the sample application zone (2) comprises at least one analyte-specific conjugate with direct or indirect label for the detection of the at least one analyte or analogue thereof. The intermediate zone (6) may or may not be present on the device and may optionally comprise at least one analyte-specific conjugate with direct or indirect label for the detection of the at least one analyte or analogue thereof.

In a particular embodiment of the present invention, the analyte detection method comprises the steps of vertically positioning the test device, applying a sample at the top of the device, allowing the sample to migrate through the sample application zone (2) and hydrate the at least one analyte-specific conjugate, allowing an at least one analyte in said sample to react with the at least one analyte-specific conjugate, thereby forming at least one complex, allowing the at least one complex to reach the non capillary zone (14), to pass by gravity the non capillary zone (14) to come in contact and migrate through the optional intermediate zone (6) and to go through the detection zone (4) thereby reacting with at least one capture reagent and allowing the development of a detectable signal thereby detecting said at least one analyte.

In a further aspect, the present invention provides an analyte detection method for the detection of at least one analyte in a sample, comprising the step of contacting an assay device with a sample, and allowing the sample to move from the top to the bottom of said device by gravity, and detecting an at least one analyte or analogue thereof, wherein said assay device is selected from the (gravity driven) test device according to the invention, test strips, dipsticks, diagnostic strip, flow through devices and lateral flow devices.

The present gravity driven test devices and methods are particularly suitable but not limited to of the detection of analytes in a sample, in particular for the detection of one or more analytes or analogues from (harmful) microorganisms comprising *Cryptosporidium parvum*, *Toxoplasma gondii*, *Giardia lamblia*, *C. difficile*, *E. coli*, *E. histolytica*, RSV (Respiratory Syncytial Virus), Influenza-A and -B viruses, Rotavirus, Adenoviruses types 40 & 41 or other Adenovirus groups, *Legionella pneumophila* urinary antigen, Coronaviruses of human and animal origin and Human Metapneumoviruses.

The gravity driven test devices and methods of the present invention, although applicable to many types of analysis, are especially advantageous when used in immunoassays or oligochromatographic rapid assays, to improve conventional solid-phase immunoassay. Moreover, devices produced in accordance with the invention are relatively easy to use, and require fewer procedural steps and less complex assay technique, by comparison with prior art assays, and also provide the additional advantage of rapid quantitative, semi-quantitative or qualitative results for testing of unknown samples. The devices are additionally adapted for advantageous use as controls, e.g., to assess the accuracy and reliability of such assays. Moreover, during manufacture, devices of the invention can be relatively easily made. Assays utilizing such devices of the invention have also been found to be highly sensitive to various levels of analytes. The foregoing advantages, as well as other advantages, will be apparent from the detailed description of the invention as set forth herein, the drawings and the examples illustrating it.

BRIEF DESCRIPTION OF THE DRAWINGS

FIG. 7 represents a cross section view (7a) and a rear view (7b) of a packaging in accordance with embodiments of the present invention.

DETAILED DESCRIPTION OF THE INVENTION

Figure 1:
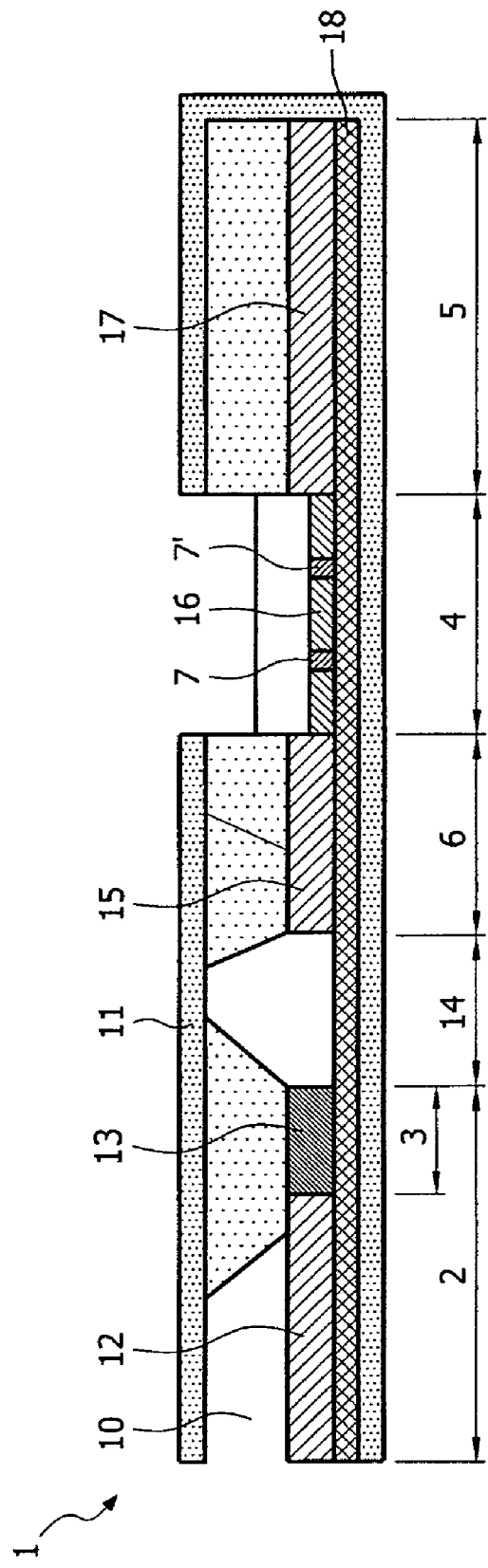
FIGS. 1, 2 and 3 represent side views in cross section of gravity driven test devices in accordance with embodiments of the present invention.

In an embodiment, the present invention provides a test device (1), also referred as a "sheet-like gravity driven test device", for the detection of at least one analyte in a sample, comprising: a solid support (18) comprising arranged from one end to the other end of the support side by side, (i) a first capillary zone being a sample receiving zone (2), (ii) a non-capillary zone (14), and (iii) a second capillary zone being a sample detection zone (4). According to the invention, the device comprises two capillary zones arranged at both end of the longitudinal axis of the support, in fluid communication with each other through a non-capillary zone, wherein a sample to be tested can flow by gravity. Said solid support can be of any suitable shape including but not limited to rectangular, square, triangle or any other shapes. Preferably said solid support (18) is substantially rectangular in shape.

According to an embodiment of the invention, the sample receiving zone of the test device comprises a sample application zone (2) and the sample detection zone comprises a detection zone (4) and optionally an intermediate zone (6) disposed next to said detection zone (4), wherein said detection zone (4) optionally comprises a control subzone. Preferably said intermediate zone (6) and said detection zone (4) are in contact with each other.

In another embodiment, said detection zone comprises an absorbent zone or region (5) disposed next to the detection zone (4) in capillary flow communication with each other.

According to a particular embodiment, the test device (1) for the detection of at least one analyte in a sample comprises: on one or more sides of the solid support (18), arranged from one end to the other end of the device:
(a) a first capillary zone comprising a sample application zone (2),
(b) a second capillary zone comprising a detection zone (4), optionally an intermediate zone (6) disposed next to said detection zone (4), and optionally an absorbent zone or region (5) disposed next to said detection zone (4), wherein said detection zone (4) optionally comprises a control subzone, and
(c) a non-capillary zone (14) separating the sample application zone (2) of the first capillary zone from the detection zone (4) or from the optional intermediate zone (6) of the second capillary zone,
wherein said sample application zone (2), said non capillary zone (14) and said detection zone (4) or said optional intermediate zone (6), are disposed in a manner such that when the device is in use, sample can flow by gravity from the sample application zone (2) to the detection zone (4) or to the optional intermediate zone (6).

According to particular embodiment, the detection zone (4) comprises at least one capture reagent specifically recognizing at least one analyte or analogue thereof; and the sample application zone (2) comprises at least one analyte-specific conjugate with direct or indirect label for the detection of at least one analyte or analogue thereof. According to a further particular embodiment the intermediate zone (6) may comprise at least one analyte-specific conjugate with direct or indirect label for the detection of at least one analyte or analogue thereof.

According to another particular embodiment, the detection zone (4) comprises at least two capture reagents specifically recognizing at least two analytes or analogues thereof; and the sample application zone (2) comprises at least two analyte-specific conjugates with direct or indirect label for the detection of at least two analytes or analogues thereof.

According to yet another particular embodiment, the detection zone (4) comprises at least three capture reagents specifically recognizing at least three analytes or analogues thereof; and the sample application zone (2) comprises at least three analyte-specific conjugates with direct or indirect label for the detection of the at least three analytes or analogues thereof.

The invention is particularly suitable for performing multiplex detection, wherein more than one analyte is detected.

As used herein, the term "test device" and "gravity driven test (GDT) device" are used interchangeably and refers to a test device, wherein the different zones of the device are disposed in a manner such that when the device is in use, sample can flow from the sample application zone (2) to the detection zone (4) by gravity through the non-capillary zone (14). The non-capillary zone (14) of device according to the invention provides for a mixing zone, allowing thereby the correct and fast mixing of the reagent resulting in improved assay accuracy and consistency. The tests using devices of the invention can be performed with rapidity even if the sample is viscous. This is in contrast to the conventional tests which take much longer to perform. Because of said non-capillary zone (14) the device can only be used in a vertical position.

Referring to FIGS. 1, 2, 3 and 4 of the drawings, particular embodiments of the gravity driven test devices of the present invention is shown generally at (1). The device (1) according to the invention is a sheet-like device, for example of a substantially rectangular shape, in particular a stick, which includes a substantially planar, flexible, rigid or semi-rigid support (18) comprising on one or more sides thereof a sample application zone (2), an optional intermediate zone (6), a detection zone (4), and optionally an absorbent zone (5), wherein the intermediate zone (6), the detection zone (4) and the absorbent zone (5) are in contact with each other. According to an embodiment of the present invention, a non capillary zone (14) separates the intermediate zone (6) from the sample application zone (2). Zone (2) is separated from zone (6), (4) and (5) by the non capillary zone (14). The zones on the solid support are provided along the longitudinal axis of the strip, next to each other. FIG. 4a illustrates the device according to a particular embodiment of the invention without intermediate zone (6). In FIG. 4a the device comprises on one or more sides of a rigid or semi-rigid support (18) a sample application zone (2), a detection zone (4), and optionally an absorbent zone (5), wherein the detection zone (4) and the absorbent zone (5) are in capillary flow communication with each other. The sample application zone (2) is provided at one end of the solid support and is separated from the detection zone (4) (FIG. 4a) or the optional intermediate zone (6) (FIG. 4a1) by a zone (14) free of any capillary material.

In an embodiment, the sample application zone (2) comprises a reactive zone (3). In a particular embodiment, the sample application zone (2) comprises one or several absorbent membrane(s) (12) referred herein as "first absorbent membrane (12)" and a conjugate area or pad (13) in the reactive zone (3). As used herein "conjugate area (13)" or "conjugate pad (13)" can be used interchangeably. The sample application zone (2) may comprise several analyte-specific conjugates in the first reactive zone (3) comprising the conjugate area or pad (13), with either direct or indirect label which allows detection of said analytes or analogues thereof. The sample application zone (2) comprises at least one analyte specific conjugate.

In an alternate embodiment, the sample application zone (2) comprises an absorbent membrane (12) and the intermediate zone (6) can comprise a reactive zone comprising a conjugate area or pad. The intermediate zone (6) may comprise several analyte-specific conjugates in the reactive zone comprising the conjugate area or pad, with either direct or indirect label which allow detection of said analytes or analogues thereof.

In a yet alternate embodiment, both said sample application zone (2) and/or the intermediate zone (6) comprise reactive zones, said reactive zones comprising conjugate area or pads comprising one or more analyte-specific conjugates with either direct or indirect label which allow detection of said analytes or analogues thereof.

In an embodiment, said sample application zone (2) may further comprise at least one control conjugate also referred as "migration control conjugate". The specific conjugate and/or migration control conjugate comprises a label selected from the group comprising, but non limited to, conjugated metallic colloids, conjugated polystyrene microspheres, carbon nanotubes and micro- or nanoparticles with a particular color, fluorescent carbon nanotubes and fluorescent micro- or nanoparticles. In an embodiment, the specific conjugate and/or migration control conjugate comprises either gold particles and/or polystyrene microspheres and/or carbon nanotubes as direct label and result in the appearance of control and test signals.

In an embodiment, the intermediate zone (6) comprises one or several absorbent membranes (15) referred herein as "second absorbent membrane (15)" and may carry one or more specific and/or control conjugates.

In an embodiment, the detection zone (4) comprises an active membrane (16) made of nitrocellulose or another matrix able to get coated by reagents that interact with other reagents located in the application zone or present in the sample to be tested. Preferably, the detection zone (4) comprises for instance nitrocellulose as active membrane (16). In an embodiment, said detection zone (4) may have a control subzone. The detection zone may comprise several capture reagents (7, 7') specifically recognizing analytes or analogues thereof to be detected in the test sample or only the control conjugate located in the conjugate area or pad (13). Capture reagents (7, 7') can be coated at different levels of the detection zone (4). Capture reagents may be either analyte-specific capture reagents (7) or control (reference) capture reagents (7'). In an embodiment of the present invention, the detection zone (4) comprises at least one control test line with at least one control capture reagent (7') specifically recognizing the control conjugate in the application zone (2) or in the intermediate zone (6).

In an embodiment of the present invention, the analyte-specific conjugate and/or the control conjugate comprise a label selected from the group comprising, but not limited to, conjugated metallic colloids, conjugated polystyrene microspheres, carbon nanotubes, microparticles with a particular color and fluorescent microparticles, preferably a direct or indirect label selected from gold particles and polystyrene microspheres.

In an embodiment the absorbent zone (5) comprises an absorbent membrane (17) referred herein as "third absorbent membrane (17)".

According to the present invention, a non-capillary zone (14) keeps apart the sample application zone (2) from the detection zone (4) or from the second absorbent membrane (15) of the intermediate zone (6) if present. Said non-capillary zone acts as a mixing zone resulting in improved assay accuracy and consistency when the device is in use. In addition the non-capillary zone allows rapid migration of the sample across the device as there are no capillary constraints to the migration of said sample. Clogging is further avoided.

Optionally, the device of the invention may be accommodated within a housing, said housing enabling at least part of the sample application zone to be in communication with the exterior of said housing such that a sample can be applied to said device, said housing further comprising a window juxtaposed over at least a portion of said device, the sample detection zone located on said portion being in visual communication with the exterior of the housing.

Optionally, the device of the invention may be embedded within a housing-like system made of specific polymers such that a sample can be applied to said device. A window can be juxtaposed over at least a portion of said device i.e. the sample detection zone located on said portion being in visual communication with the exterior of the polymer embedment.

FIGS. 1 and 4a3 and 2a particularly show different embodiments wherein the device (1) is involved in hollow or heat-molded casing or housing (11). Typically, said housing (11) comprises a hollow casing construction, and is made from a moisture impervious solid material such as a suitable plastic material, for example. The housing (11) enabling at least part of the sample application zone (2) to be in direct communication with the exterior of said housing (11) such that said sample can be applied to said device (1) through the casing receiving area (10).

The housing (11) further comprises a window juxtaposed over at least a portion of the device (1) so that at least the detection zone (4) comprised in said device (1) is in visual communication with the exterior of the housing (11). Said window can be of any suitable shape so as to allow clear viewing of at least the detection zone (4). In an embodiment, said window can be rectangular in form, preferably having a width slightly narrower than that of the device (1).

FIGS. 2b, 4a, 4a1, 4a2 and 3 show different embodiments of the present invention, wherein the device (1) is without hollow casing (11). FIGS. 2b, 4a2 and 3 illustrate a device (1) according to embodiments of the invention wherein a sticker (20) may cover the sample application zone (2), the non-capillary zone (14) (so as to form a space wherein the sample can move freely by gravity), and the intermediate zone (6) and overlaps partially the detection zone (4). A second sticker (21) may also cover the absorbent zone (5). The stickers (20, 21) may be used to force the liquid to move into the different membranes (12, 13, 15, 16, 17), without escaping from the stick surface. In an alternative embodiment, the device (1) described in FIGS. 2b and 3 can be wrapped by a sticker or within a heat-molded plastic tube or embedded in a specific polymer to avoid any liquid leakages on the sides of the stick. FIGS. 4a and 4a1 show a device (1) according to embodiments of the present invention without hollow casing and without stickers.

Referring to FIG. 1, a device (1) according to an embodiment of the invention is illustrated comprising a support (18) comprising on one side thereof a sample application zone (2), a non capillary zone (14), an intermediate zone (6), a detection zone (4), and an absorbent zone (5), wherein the intermediate zone (6), the detection zone (4) and the absorbent zone (5) are in contact with each other. The sample application zone (2) is separated from the intermediate zone (6) by the non capillary zone (14). The zones on the solid support are provided along the longitudinal axis of the strip, next to each other. The sample application zone (2) comprises a reactive zone (3) located at one end of said sample application zone (2). In particular, the sample application zone (2) comprises a first absorbent membrane (12) and a conjugate area or pad (13) in the reactive zone (3) of said sample application zone (2). The intermediate zone (6) comprises a second absorbent membrane (15). In an embodiment, said conjugate area or pad (13) carries one or more specific and/or control conjugates. In another embodiment, said second absorbent membrane (15) carries one or more specific and/or control conjugates. In a third embodiment, both said conjugate pad (13) and said second absorbent membrane (15) carry one or more specific and/or control conjugates. The detection zone (4) comprises an active membrane (16) comprising analyte-specific capture reagent (7) and a control (reference) capture reagent (7'). The absorbent zone (5) comprises absorbent membrane (17). The device (1) is accommodated within a housing (11) enabling at least part of the first absorbent membrane (12) to be in direct communication with the exterior of said housing (11) such that a sample can be applied to said device (1) through the casing receiving area (10).

Figure 2A:
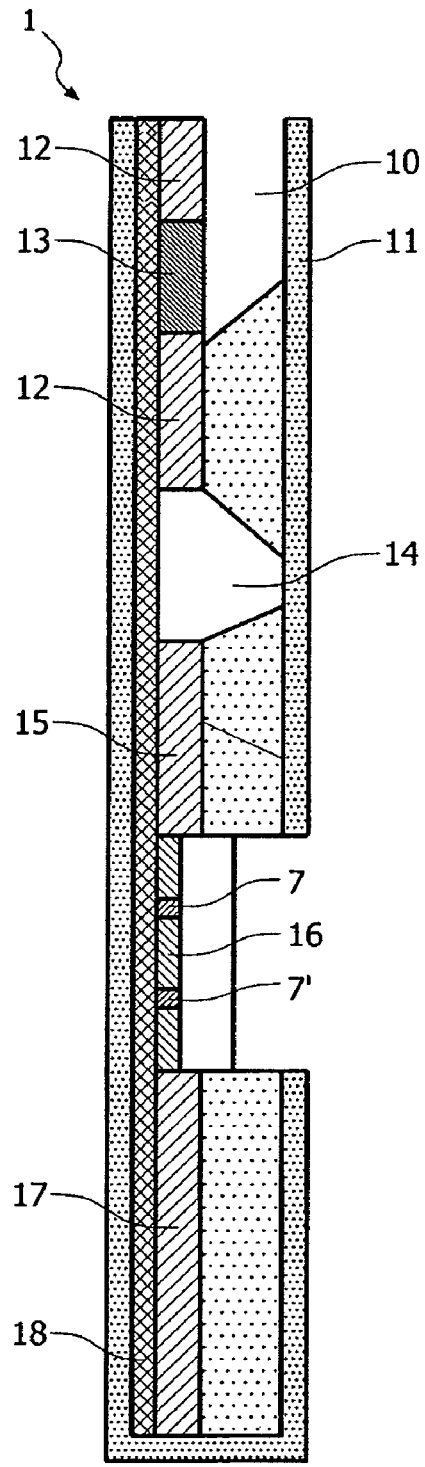

Referring to FIG. 2a, a device (1) according to another embodiment of the invention is illustrated comprising: a support (18) comprising on one side thereof, from one end of the device to the other end of the device, a first absorbent membrane (12) provided on both sides of a conjugate area or pad (13), a non capillary zone (14), a second absorbent membrane (15), an active membrane (16) comprising analyte-specific capture reagent (7) and a control (reference) capture reagent (7') and a third absorbent membrane (17). The second absorbent membrane (15), the active membrane (16) and the third absorbent membrane (17) are in contact with each other. The first absorbent membrane (12) is separated from the second absorbent membrane (15) by the non capillary zone (14). The membranes and pads on the solid support are provided along the longitudinal axis of the strip, next to each other. In an embodiment, said conjugate area or pad (13) carries one or more specific and/or control conjugates. In another embodiment, said second absorbent membrane (15) carries one or more specific and/or control conjugates. In a third embodiment, both said conjugate area or pad (13) and said second absorbent membrane (15) carry one or more specific and/or control conjugates. The device (1) is accommodated within a housing (11) enabling at least part of the first absorbent membrane (12) to be in direct communication with the exterior of said housing (11) such that a sample can be applied to said device (1) through the casing receiving area (10).

Figure 2B:
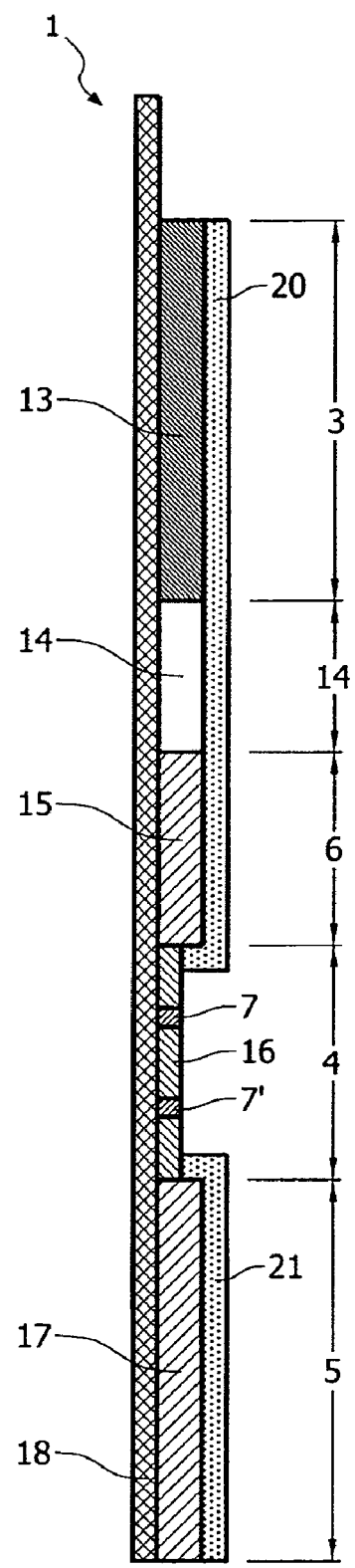

Referring to FIG. 2b, a device (1) according to yet another embodiment of the invention is illustrated comprising a support (18) comprising on one side thereof a reactive zone (3), a non capillary zone (14), an intermediate zone (6), a detection zone (4), and an absorbent zone (5), wherein the intermediate zone (6), the detection zone (4) and the absorbent zone (5) are in contact with each other. The reactive zone (3) is separated from the intermediate zone (6) by the non capillary zone (14). The zones on the solid support are provided along the longitudinal axis of the strip, next to each other. The reactive zone (3) comprises a conjugate are or pad (13). The intermediate zone (6) comprises a second absorbent membrane (15). In an embodiment, said conjugate area or pad (13) carries one or more specific and/or control conjugates. In another embodiment, said second absorbent membrane (15) carries one or more specific and/or control conjugates. In a third embodiment, both said conjugate area or pad (13) and said second absorbent membrane (15) carry one or more specific and/or control conjugates. The detection zone (4) comprises an active membrane (16) comprising analyte-specific capture reagent (7) and a control (reference) capture reagent (7'). The absorbent zone (5) comprises absorbent membrane (17). A sticker (20) covers the reactive zone (3), the non-capillary zone (14), and the intermediate zone (6) and overlaps partially the detection zone (4). A second sticker (21) covers the absorbent zone (5).

Figure 3:
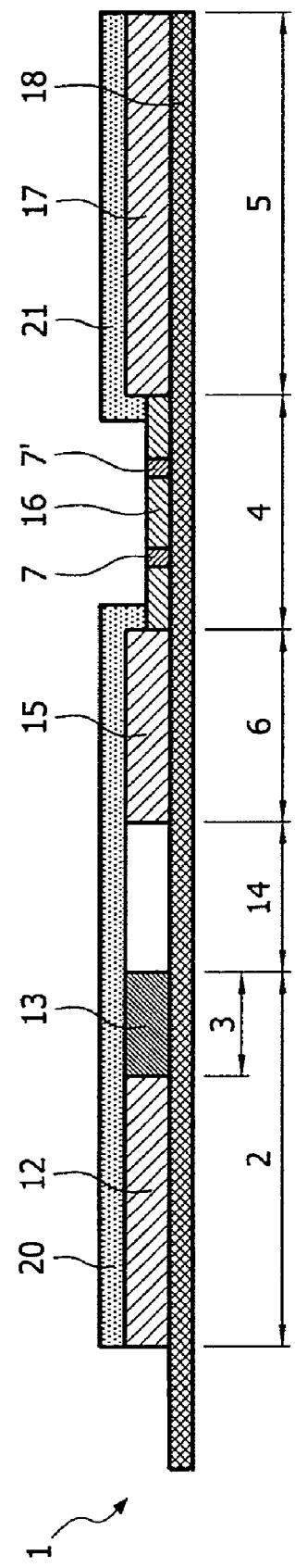
Figure 4:
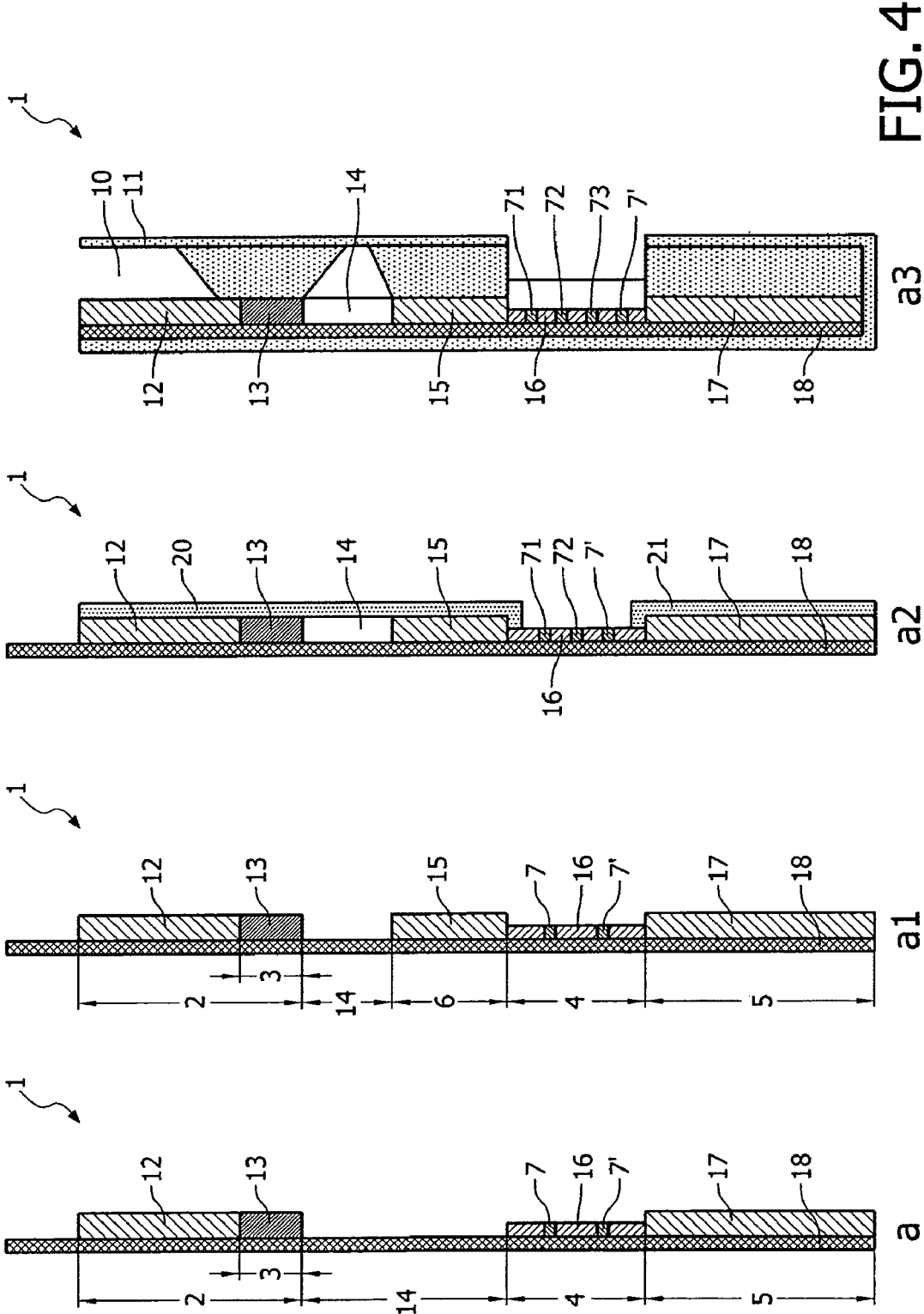
FIG. 4 represents side views in cross section (4a, 4a1, 4a2, 4a3) and front views (4b, 4c, 4d and 4e) of gravity driven test devices in accordance with embodiments of the present invention.
Figure 4:
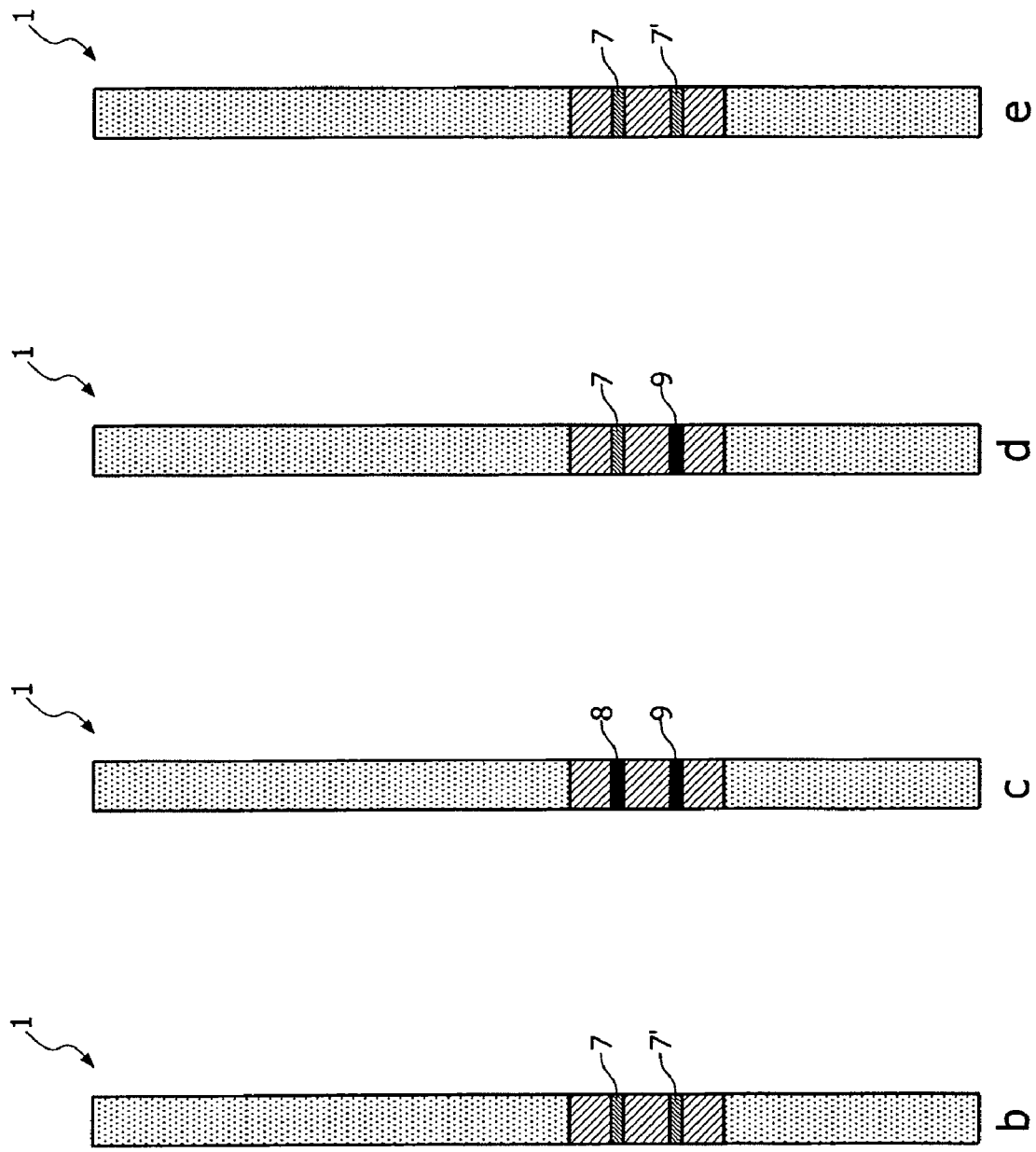

Referring to FIG. 3, a device (1) according to a further embodiment of the invention is illustrated. Said device (1) comprises a support (18) comprising on one side thereof a sample application zone (2), a non capillary zone (14), an intermediate zone (6), a detection zone (4), and an absorbent zone (5), wherein the intermediate zone (6), the detection zone (4) and the absorbent zone (5) are in contact with each other. The sample application zone (2) is separated from the intermediate zone (6) by the non capillary zone (14). The zones on the solid support are provided along the longitudinal axis of the strip, next to each other. The sample application zone (2) comprises a reactive zone (3) located at one end of said sample application zone (2). In particular, the sample application zone (2) comprises a first absorbent membrane (12) and a conjugate area or pad (13) in the reactive zone (3) of said sample application zone (2). The intermediate zone (6) comprises a second absorbent membrane (15). In an embodiment, said conjugate area or pad (13) carries one or more specific and/or control conjugates. In another embodiment, said second absorbent membrane (15) carries one or more specific and/or control conjugates. In a third embodiment, both said conjugate area or pad (13) and said second absorbent membrane (15) carry one or more specific and/or control conjugates. The detection zone (4) comprises an active membrane (16) comprising analyte-specific capture reagent (7) and a control (reference) capture reagent (7'). The absorbent zone (5) comprises absorbent membrane (17). A sticker (20) covers the reactive zone (3), the non-capillary zone (14), and the intermediate zone (6) and overlaps partially the detection zone (4). A second sticker (21) covers the absorbent zone (5).

FIG. 4a illustrates a device (1) according to a particular embodiment of the invention without intermediate zone (6) and without hollow casing and stickers. In FIG. 4a, the device (1) comprises a support (18) whereon is provided a sample application zone (2), a non capillary zone (14), a detection zone (4), and an absorbent zone (5), wherein the detection zone (4) and the absorbent zone (5) are in contact with each other. The sample application zone (2) is separated from the detection zone (4) by the non capillary zone (14). The zones on the solid support are provided along the longitudinal axis of the strip, next to each other. The sample application zone (2) comprises a reactive zone (3) located at one end of said sample application zone (2). In particular, the sample application zone (2) comprises a first absorbent membrane (12) and a conjugate area or pad (13) in the reactive zone (3) of said sample application zone (2). Said conjugate area or pad (13) carries one or more specific and/or control conjugates. The detection zone (4) comprises an active membrane (16) comprising analyte-specific capture reagent (7) and a control (reference) capture reagent (7'). The absorbent zone (5) comprises absorbent membrane (17).

FIG. 4a1 illustrates a device (1) according to a particular embodiment of the invention without hollow casing and stickers. In FIG. 4a1, the device (1) comprises a support (18) whereon is provided a sample application zone (2), a non capillary zone (14), an intermediate zone (6), a detection zone (4), and an absorbent zone (5), wherein the intermediate zone (6), the detection zone (4) and the absorbent zone (5) are in contact with each other. The sample application zone (2) is separated from the intermediate zone (6) by the non capillary zone (14). The zones on the solid support are provided along the longitudinal axis of the strip, next to each other. The sample application zone (2) comprises a reactive zone (3) located at one end of said sample application zone (2). In particular, the sample application zone (2) comprises a first absorbent membrane (12) and a conjugate area or pad (13) in the reactive zone (3) of said sample application zone (2). The intermediate zone (6) comprises a second absorbent membrane (15). In an embodiment, said conjugate area or pad (13) carries one or more specific and/or control conjugates. In another embodiment, said second absorbent membrane (15) carries one or more specific and/or control conjugates. In a third embodiment, both said conjugate pad (13) and said second absorbent membrane (15) carry one or more specific and/or control conjugates. The detection zone (4) comprises an active membrane (16) comprising analyte-specific capture reagent (7) and a control (reference) capture reagent (7'). The absorbent zone (5) comprises absorbent membrane (17).

FIG. 4a2 illustrates a device (1) according to a particular embodiment of the invention for performing multiplex assays. The device (1) comprises a support (18) whereon is provided a sample application zone (2), a non capillary zone (14), an intermediate zone (6), a detection zone (4), and an absorbent zone (5), wherein the intermediate zone (6), the detection zone (4) and the absorbent zone (5) are in contact with each other. The sample application zone (2) is separated from the intermediate zone (6) by the non capillary zone (14). The zones on the solid support are provided along the longitudinal axis of the strip, next to each other. The sample application zone (2) comprises a reactive zone (3) located at one end of said sample application zone (2). In particular, the sample application zone (2) comprises a first absorbent membrane (12) and a conjugate area or pad (13) in the reactive zone (3) of said sample application zone (2). The intermediate zone (6) comprises a second absorbent membrane (15). In an embodiment, said conjugate area or pad (13) carries two or more specific and/or control conjugates. In another embodiment, said second absorbent membrane (15) carries two or more specific and/or control conjugates. In a third embodiment, both said conjugate area or pad (13) and said second absorbent membrane (15) carry two or more specific and/or control conjugates. The detection zone (4) comprises an active membrane (16) comprising at least two analyte-specific capture reagents (71, 72) and a control (reference) capture reagent (7'). The absorbent zone (5) comprises absorbent membrane (17). A sticker (20) covers the reactive zone (3), the non-capillary zone (4), and the intermediate zone (6) and overlaps partially the detection zone (4). A second sticker (21) covers the absorbent zone (5).

FIG. 4a3 illustrates a device (1) according to a particular embodiment of the invention for performing multiplex assays. The device (1) comprises a support (18) whereon is provided a sample application zone (2), a non capillary zone (14), an intermediate zone (6), a detection zone (4), and an absorbent zone (5), wherein the intermediate zone (6), the detection zone (4) and the absorbent zone (5) are in contact with each other. The sample application zone (2) is separated from the intermediate zone (6) by the non capillary zone (14). The zones on the solid support are provided along the longitudinal axis of the strip, next to each other. The sample application zone (2) comprises a reactive zone (3) located at one end of said sample application zone (2). In particular, the sample application zone (2) comprises a first absorbent membrane (12) and a conjugate area or pad (13) in the reactive zone (3) of said sample application zone (2). The intermediate zone (6) comprises a second absorbent membrane (15). In an embodiment, said conjugate area or pad (13) carries three or more specific and/or control conjugates. In another embodiment, said second absorbent membrane (15) carries at least three specific and/or control conjugates. In a third embodiment, both said conjugate area or pad (13) and said second absorbent membrane (15) carry three or more specific and/or control conjugates. The detection zone (4) comprises an active membrane (16) comprising three analyte-specific capture reagents (71, 72, 73) and a control (reference) capture reagent (7'). The absorbent zone (5) comprises absorbent membrane (17). The device (1) is accommodated within a housing (11) enabling at least part of the first absorbent membrane (12) to be in direct communication with the exterior of said housing (11) such that a sample can be applied to said device (1) through the casing receiving area (10).

The device of the invention preferably is an immunogravity driven test device. In an embodiment of the present invention, FIGS. 4b to 4e illustrate schematically the manner in which results may be indicated on such a device (1) i.e.: FIG. 4b shows the device (1) before testing wherein the sample detection zone comprises one analyte-specific capture reagent (7) and a control (reference) capture reagent (7'). FIG. 4c shows a positive result wherein complexes are formed between the analyte-specific conjugates and the analytes detected, and a colored line (8) is thereby generated at the sample detection zone where the capture reagent (7) specifically recognizes the complexes. The reaction between control capture reagent (7') and reference conjugate gives rise to a control line (9). FIG. 4d shows a negative result, wherein there is no analytes detected and therefore no colored line (8) and reaction between control capture reagent (7') and reference conjugate gives rise to a control line (9). FIG. 4e shows an invalid result, wherein there is no reaction between control capture reagent (7') and reference conjugate, and therefore no control line (9).

In a preferred embodiment, when the device is in use, in case of a positive reaction, i.e. in case one or more complexes are formed between the analyte-specific conjugates and the analytes to be detected, a specific signal is generated at the detection zone (4) where the capture reagent (7) is deposited. The capture reagent (7) specifically recognizes the complexes to generate a colored line (8). In a preferred embodiment, the reaction between control capture reagent (7') and reference conjugate gives rise to a control line (9) visible in the detection zone (4).

As described above, according to an embodiment of the invention, the detection zone (4) of the device (1) can be sensitized with one or more test reagents (analyte-specific capture reagents) (7) and with migration control capture reagent(s) (control capture reagents) (7'). The test reagent (7) is aimed at the direct or indirect detection of the analyte to be detected in the sample, and the migration control capture reagent (7') is directed either against an anti-analyte antibody that is coupled to a direct label, either against a specific conjugate non relevant to the analytes to be detected.

The capture reagents (7, 7') and conjugate reagents are preferably immunoreagents, oligonucleotides, ligand or receptor molecules or analogues thereof. The capture reagents (7, 7') and conjugate reagents can be selected from the group comprising oligonucleotides or analogues thereof, polyclonal or monoclonal antibodies or hypervariable antibody fragments, or an antigen recognized by serological compounds such as IgG, IgA, IgE and IgM or one of the specific reagents of couples (ligand-receptor) like biotin-streptavidin, and the like.

The detection label is preferably a direct particulate label, in particular a direct label selected from the group comprising conjugated metallic colloids, conjugated polystyrene microspheres, micro- or nanoparticles or nanotubes with a particular color, and fluorescent micro- or nanoparticles or fluorescent nanotubes.

The present invention in particular relates to a gravity driven test device (1) composed of polymeric substances laminated on a rigid or semi-rigid solid support (18) made of polymer. In a particular embodiment, the rigid solid support (18) is a plastic backing such as a plastic. The present devices advantageously allow the detection of different analytes or analogues thereof, which could react differently on the active membrane (16).

In a particular embodiment, the membranes of the sample application zone (2) are made of glass fibers with the first reactive zone (3) made of polyester or another matrix. In a particular embodiment, the membrane of the detection zone (4) is made of nitrocellulose, the membrane of the intermediate zone (6) is made of glass fibers, polyester or cellulose and the membrane of the absorbent zones (5) is made of cellulose. The sample application zone (2) and first reactive zone (3) may be made of the same material. Alternatively, the conjugates may be impregnated directly onto the sample application zone (2).

The device (1) of the invention is highly suitable for the detection of several analytes or analogues thereof potentially present in a test sample such as a solution or biological sample. The analytes or analogues thereof may be obtained from or may be produced by (harmful) microorganisms such as but not limited to *Cryptosporidium parvum, Toxoplasma gondii, Giardia lamblia, C. difficile, C. difficile* toxins, *E. coli, E. histolytica*, RSV (Respiratory Syncytial Virus), Influenza-A and -B viruses, Rotavirus, Adenoviruses types 40 & 41 or other Adenovirus groups, *Legionella pneumophila* urinary antigen, Coronaviruses of human and animal origin and Human Metapneumoviruses.

In a preferred embodiment of the invention, more than one analyte or analogue thereof is detected with one device according to the invention. The gravity driven test device (1) of the present invention is highly suitable for multiplex detection. For instance, it is possible to detect the presence of Influenza A and Influenza B or Adenovirus and RSV on the same device. Rotavirus and enteric Adenoviruses detection or *C. parvum, C. difficile* toxins, *G. lamblia* and *E. histolytica* detection are other examples.

A particular embodiment of the invention concerns a sheet-like immunogravity driven test device (1) comprising on a rigid or semi-rigid solid support (18): a sample application zone (2) optionally with a conjugate area or pad (13), a non-capillary zone (14), an optional intermediate zone (6) and a detection zone (4) possibly with a control subzone, and optionally an absorbent zone (5). The detection zone (4) of the device (1) is sensitized with a test reagent (7). It is also sensitized with a control antibody (7'). The non-capillary zone (14) avoids any direct and capillary contact between the sample application zone and the sample detection zone, capillary contact which is usually observed and described in prior art devices.

Preferably, the conjugates are dried in the lower part of the sample application zone on the first reactive zone (3).

In a particular embodiment, antibodies are used in the detection zone (4). Preferably, the control antibody or antibodies, in particular the migration control antibodies (7'), are coated in a control region of the detection zone (4), said control region being positioned below a test region in which a test antibody, in particular an analyte-specific antibody is coated. As indicated above, the test and control conjugates may be reagents such as oligonucleotides or analogues thereof or polyclonal or monoclonal antibodies or such as hypervariable antibody fragments or such as an antigen recognized by serological compounds such as IgG, IgA, IgE and IgM or one of the specific reagents of couples like biotin-streptavidin. The label of the test or specific conjugates and of the control conjugates may be a direct label, in particular a direct label that is selected from the group consisting of conjugated metallic colloids, conjugated polystyrene particles and micro- or nanoparticles or nanotubes having a specific particular color or being fluorescent.

Advantageously, the control conjugates present in the device (1) of the present invention do not interfere with the detection of the analytes or analogues thereof suspected to be present. The controls advantageously generate a signal with constant intensity that is independent of the specific signal. Said control(s) may allow to quantify or semi-quantify the detected analyte(s) or analogue(s) thereof.

A sheet-like gravity driven test device (1) according to the invention is easy to use and handle and is highly flexible in its use. The gravity driven test device (1) of the invention allows for instance the use of different kinds of particles and/or different kinds of sample and/or conjugates pads on the same device (1). The present invention therefore provides devices (1) which are easy to handle and which allow rapid but accurate detection and/or diagnosis of multiple analytes in a test sample (multiplex detection).

A particular embodiment of the invention relates to a gravity driven test device (1) according to the invention wherein a porosity of the active membrane (16) of 8, 10, 12, 15 µm etc may be chosen.

Another embodiment of the present invention concerns a gravity driven test device (1), wherein the active membrane (16) is made of different materials, with similar or different porosities. For instance, the active membrane may be comprised of nitrocellulose or of Predator™ (Pall) or of Porex membrane. The person skilled in the art is aware of other possibilities. Possible active membranes (16) for use in the detection zone (4) include but are not restricted to: cellulose, nitrocellulose, cellulose acetate, glass fibers, nylon, acrylic copolymer/nylon, polyethersulfone, polyethylene and polyester.

The present invention further relates to detection methods that make use of one of the above described gravity driven test devices, which can be used to check the presence of analytes or analogues thereof. Detection can be performed via the naked eye and/or automatically with the aid of a stripreader and specific software programs for the detection and/or quantification of analytes or analogues thereof.

A particular embodiment of the invention concerns a method as described above wherein the development or not of a signal (for instance a colored signal) at the position of the immobilization of the test or analyte-specific capture reagent (7), such as a test or analyte-specific antibody, indicates the presence or absence of an analyte or analogue thereof.

Advantageously, the development of a signal (for instance a colored signal) at the position of the immobilization of the control capture reagent (7'), such as a migration control antibody, indicates that the sample has moved on the active membrane of the (immuno)gravity driven test device (1) according to the invention.

Advantageously, the development of a signal (for instance a colored signal) at the position of the immobilization of the control reagent, such as a control antibody, indicates the correct use and good condition of the sheet-like (immuno) gravity driven test device (1) according to the invention, the quality of the dried conjugates as well as the completion of the capture reaction such as an immunological reaction.

Advantageously, the development of a signal (for instance a colored signal) at the position of the immobilization of a control capture reagent (migration and possibly reference control reagent), such as a control antibody, is independent of the presence or absence of the analyte or analogue thereof to detect in the sample.

The present invention therefore provides new devices for rapid detection of analyte or analogue thereof and their use in the detection of (multiple) analytes or analogues thereof possibly present in a test sample such as a biological sample. The devices according to the invention show better reactivity than prior art devices. Having a non-capillary zone and having a gravity driven migration, allows handling a variety of samples including culture supernatants, biological fluids such as nasopharyngeal secretions, blood, serum, urine, semen, saliva, or excrement. In particular the device of the invention allow the testing of viscous type of samples, as such as stool specimens, slurries, colloids and the like without clogging. The present device in use allows fast migration of the sample across the device independently of the sample viscosity or complexity. Preferred devices comprise on one or more sides of a supporting polymer (18) a sample application zone (2), a non-capillary zone (14), an intermediate zone (6), a detection zone (4), and an absorption zone (5). The detection zone (4) may contain several defined subzones, preferably lines, each dedicated to the detection of one or more particular analytes, a group of analytes or of particular analyte products. There may be included at least one control zone. The devices of the invention may be one-piece sheet-like devices or may be comprised of several parts in contact with each other.

Prior art documents such as EP 0 088 636, EP 0 186 799, EP 0 284 232 and WO 88/08534 are referenced to with respect to the principles of (immuno)chromatographic devices and the reaction between the different compounds such as analyte, conjugate and capture reagent such as an immunoreagent.

The disclosure of these documents is herein incorporated in their entirety by reference thereto.

The devices (1) according to the invention are composed of porous polymeric substances that preferably are laminated on one or more sides of the rigid or semi-rigid polymer (18) to provide mechanical strength, which makes the devices (1) of the invention easy to handle. The porosity of the polymeric substances should be such that movement of a fluid and its components from the top to the bottom of the stick, moving along rehydrated conjugate is possible without any hindrance because of gravity forces. These characteristics are also allowed by the hydrophilic properties of these polymers. Examples of suitable polymers are cellulose, nitrocellulose, cellulose acetate, glass fibers, nylon, acrylic copolymer/nylon, polyethersulfone, polyethylene and polyester.

The term "analytes or analogues thereof" or "analytes" are used interchangeably, and relates to molecules to be detected in biological samples and analogues and derivatives thereof when such analogues and derivatives bind another molecule used in the assay in a manner substantially equivalent to that of the analyte itself. Non-limiting examples of such molecules include proteins, glycoproteins, lipoproteins, peptides, glycopeptides, haptens, polysaccharides, lipopolysaccharides, nucleic acids, viral particles, parts of micro-organisms such as bacteria, viruses, protozoans and parasites, or chemical compounds of any origin.

The devices (1) according to the invention are in particular useful for the detection of harmful microorganisms or compounds thereof in biological samples, including but not limited to the detection of *Cryptosporidium parvum* oocysts, *Giardia lambila* cysts, RSV (Respiratory Syncytial Virus), *E. coli*, *C. difficile*, *C. difficile* toxins, *E. histolytica*, Influenza-A and -B viruses, Rotavirus, Adenoviruses types 40 & 41, Adenovirus groups, *Legionella pneumophila* urinary antigens, Coronaviruses of human and animal origin and Human Metapneumoviruses. Advantageously, the device can be designed that allows detection of several such analytes or analogues thereof via one single test (1) and/or allows detection of more than one harmful compound produced by a given analyte such as *E. coli* shiga-like toxins I and 11, and/or allows detection of multiple serological compounds such as IgG, IgA and IgM raised after an infection by a pathogen.

The test sample, preferably a liquid test sample, suspected to contain an analyte or analogue thereof, may be derived from any biological sample, including but not limited to culture supernatants, nasopharyngeal secretions, stool specimens, serum, . . . . Samples such as for instance stool specimens are prior to application preferably suspended in a solution that allows migration of the liquid through the device (1). Samples which can be tested with the system of the present invention include biological samples such as blood, urine, semen, saliva, or excrement, preferably from a human subject. Samples from animals, plants, food, water, sewages and soil can also be tested.

Specific labeled reagents that are specific for the analytes or analogues thereof serve to detect and/or quantify analytes or analogues thereof possibly present in a sample. The specific labeled reagents (conjugates) will individually form a complex with individual analytes or analogues thereof, which complexes are then captured by analyte-specific reagents (7). A labeled reagent may be used to react finally with a control reagent adsorbed preferably onto the second porous region or zone. The capture reagents (7, 7') may be oligonucleotides or analogues, or polyclonal or monoclonal antibodies or any hypervariable antibody fragments known in the art or an antigen recognized by serological compounds such as IgG, IgA, IgE and IgM or one of the specific reagent of couples like biotin-streptavidin. Preferably monoclonal antibodies or hypervariable fragments thereof are used. Some capture reagents (7, 7') may be produced via genetic engineering.

Labeled reagents or detection agents are immobilized (impregnated) on an inert material that can be glass fibers or polyester or any other material physically and chemically inert and with sufficient porosity and wettability to allow particle movement and to allow labeled reagents to rehydrate easily and completely when liquid sample reaches them. When the liquid sample is in contact with these rehydrated detection agents, individual analytes will form a complex with their specific labeled reagent and these complexes will react with their specific reagents adsorbed on the sample detection zone while the labeled control agent will move freely up to the control reagent adsorbed onto the control zone to react therewith.

Various detection systems are known in the art. Colored or visible (direct) particulate labels known in the art include but are not limited to particles made of polystyrene (latex) polymers, metallic colloids such as gold, carbon, liposomes, silver, copper, . . . which can be conjugated to the binding reagent that normally reacts with the analytes to be detected. Detection systems for fluorescence can also be used. Quantification and/or semi-quantification are possible.

The present invention relates to a method for rapid and specific identification of several pathogens from biological samples, or laboratory samples with sheet-like gravity driven test device according to the invention (1).

In a preferred embodiment of the invention specific and control conjugates comprise visible (direct) labels to which reagents specific to analytes or analogues thereof or control reagents are bound (conjugated therewith). The complex formed between the analytes or analogues thereof or control reagent and their conjugates will move by gravity to the intermediate zone (6) before encountering the membrane of the detection zone (preferably nitrocellulose) (4) and reach specific analytes or analogues thereof or control reagents (7, 7') coated thereon. The reaction between the complexes and the reagents (7, 7') to the analytes or analogues thereof or control reagent will be visualized since the particles will accumulate and generate a visible signal (8, 9). This signal allows the user to identify specifically which analyte or analogue thereof is present in the analyzed sample and preferably also to quantify or semi-quantify (possibly via a control line (9)) the amount thereof present in the test sample.

Below, more details are provided with respect to general aspects and preferred compositions and build-up of the particular gravity driven test device according to the present invention.

To conduct the gravity driven test assay, the device (1) according to an embodiment of the invention is preferably divided into five zones, side by side Juxtaposed) longitudinally, including a sample application zone (2), a non-capillary zone (14), possibly an intermediate zone (6), a detection zone (4) and possibly an absorbent zone (5) located on one or more sides of the device (1).

In a preferred embodiment, the membranes of the sample application zone (2) are made of glass fibers or cellulose with conjugate pads (13) made of polyester, the membranes of the intermediate zone (6) are made of glass fibers or cellulose and the membranes of the detection zone (4) are made of nitrocellulose, and the membranes of the absorbent zones (5) are made of cellulose. In particular embodiments, sample application zones (2) and conjugate pads (13) can be made of the same matter or material. The conjugates can, however, also be impregnated directly onto the sample application zone (2).

The first reaction zone (3) can be fully or partially covered by the first absorbent membrane (12). Both absorbent membranes and conjugate pad could be made of the same matter or material. Possibly, in this case, the conjugates could be directly sprayed onto the polymer that is also used to absorb the sample liquid in the first absorbent membrane (12).

The conjugate pads are impregnated with particles that are coated with some compounds that could include proteins, glycoproteins, lipoproteins, peptides, glycopeptides, haptens, polysaccharides, lipopolysaccharides, nucleic acids or analogues (PNA, LNA, . . . ) to form an analyte-specific conjugate. These compounds will react somewhere specifically with analytes or analogues thereof that could be present into the sample(s) to be analyzed. Examples of suitable particles include but are not limited to colloidal gold particles; colloidal sulphur particles; colloidal selenium particles; colloidal barium sulfate particles; colloidal iron sulfate particles; metal iodate particles; silver halide particles; colloidal silver, colloidal palladium, colloidal platinum, colloidal rhodium, silica particles; colloidal metal (hydrous) oxide particles; colloidal metal sulfide particles; colloidal lead selenide particles; colloidal cadmium selenide particles; colloidal metal phosphate particles; colloidal metal ferrite particles; carbon nanotubes; any of the above-mentioned colloidal particles coated with organic or inorganic layers; protein or peptide molecules; liposomes; colored microparticles, colored nanoparticles, fluorescent micro- and nanoparticles or organic polymer polystyrene particles. In a preferred embodiment, particles are colloidal gold particles or polystyrene (latex) microspheres. Colloidal gold particles could be of about 5 to about 60 nm of diameter. Preferably, particles of about 20 nm or about 40 nm diameter are used. Polystyrene (latex) microspheres that have been activated with several chemical functions such as carboxyl one, amine one, hydroxyl one and sulfhydryl one could be used. In one preferred embodiment, non-activated and amine activated polystyrene microspheres are used. Preferably, microspheres of about 20 nm to 1000 nm and preferably from 150 nm to about 350 nm diameter are used.

In order to perform multicolor detections, different colored microspheres are used (e.g. red for analyte A, blue for analyte B and green for control line).

Analyte-specific particles to be used in the sheet-like gravity driven test devices (1) of the invention are coated with compounds that specifically bind directly or indirectly with the analyte or analogue thereof to be detected.

The detection zone (4) of the sheet-like gravity driven test devices (1) according to the invention could be made of cellulose, nitrocellulose, cellulose acetate, glass fibers, nylon, acrylic copolymer/nylon, polyethersulfone, polyethylene and polyester but preferably is made of nitrocellulose from Advanced Microdevices Pvt, Ltd. Membranes from other supplier (Schleicher & Schuell or Millipore or Porex or Pall or Whatman) can also be used.

Coating preferably is performed by diluting the reagents (7, 7') in an appropriate buffer and by distributing them onto the membrane, preferably nitrocellulose (16), with a contact system (e.g. IsoFlow from Imagen Technology). Speed distribution could vary from about 50 mm to about 10 mm/sec but is preferably fixed to about 40 mm/sec or even better at about 30 mm/sec. Volume of material distributed varies from about 0.5 to about 3 µl/cm, preferably from about 0.7 to about 2 µl/cm and more precisely from about 1 to about 2 µl/cm.

Reagent concentration varies from about 0.1 to about 10 mg/ml and preferably is about 0.15 to 2 mg/ml. In a preferred embodiment of the invention, the buffer used for this coating consisted of a saline solution (NaCl) buffered with phosphate at about pH 7.2.

In an embodiment of the invention, the sheet-like gravity driven test devices (1) of the invention include absorbent zones (5) that aspirate solution that has been transported to the end of the nitrocellulose (16). Examples of substances include cellulose and glass fibers. Cellulose (MDI) or glass fiber (Schleicher & Schuell) have been preferably used.

The sheet-like gravity driven test devices (1) of the invention, preferably also include control subzones (amongst other internal control and/or migration control) preferably containing at least one control line. The migration control conjugate should not react with the specific conjugates, nor with the analyte itself, nor with anything that could be present in the sample to be analyzed. Preferably the migration control line is built in such a way that its intensity is always the same and does not depend on the specific signal and its intensity. Coating of the control reagent is as described above. The migration capture conjugate is either mixed in the conjugate pad with the specific conjugates, either impregnated alone.

The gravity driven test device is preferably put vertically (i.e. in an upright position) in a holder, support or an empty test tube.

As used herein the term "vertically" refers to a substantially upright position. When the device is vertically positioned, the stick to be used in the present invention can make an angle varying from 45° to 135° from a horizontal plane, preferably from 60° to 120°, preferably from 80° to 100°. Liquid sample containing the analyte or analogue thereof to be detected is settled at the top of the device (1) and migrates through the first absorbent membrane (12) to the conjugate pad (13) and rehydrates both conjugates, i.e. the specific analyte or analogue thereof conjugates and the control conjugate. If related analytes or analogues thereof are present, several complexes will be formed. They will reach the non-capillary zone (14) where they are mixed. Since the liquid progresses by gravity, it passes through the second absorbent membrane (15) to come through the active membrane (16) preferably made of nitrocellulose. The said complexes will give rise to visible (e.g. red, blue, green, . . . ) lines or subzones in case of positive reactions, while the control conjugate proceeds on one's way to reach and react with its coated reagent leading to a visible colored line (green). The control signal indicates amongst others that the test has been properly performed, appearing also in the absence of a specific reaction. The control signal may further serve as a quantitative reference. Specific and control signals can be of the same or a different color. Size of particles of the control conjugates and of the specific conjugates can be the same or can be different. In a particular embodiment according to this invention, both (control and specific) conjugates, preferably gold conjugates, are impregnated into a solid inert membrane that could be polyester or nylon. Polyester is preferred. The polyester membranes used here have a size of 27×260 mm and are from Advanced Microdevices Pvt, Ltd (India). The membranes are impregnated with the preferably gold conjugates after a dilution step in a specific buffer to provide an optimal rehydratation with the liquid sample when the test is running. AccuFlow G membranes from Schleicher & Schuell are also useful for this purpose and give the advantage that the conjugates are directly sprayed onto the absorbent membrane.

In another particular embodiment according to this invention, both (control and specific) conjugates, preferably polystyrene colored microspheres, are impregnated into a solid inert membrane that could be polyester or glass fibers. Glass fibers are preferred. The glass fibers membranes used here have a size of 27×260 mm and are from Whatman.

When using the polyester membranes from Advanced Microdevices Pvt, the membranes are impregnated by dipping into an appropriate vial with a finite volume that is 1.6 ml but that could be reduced to 1.3 ml depending on the impregnation system used. Membranes are let to dry at room temperature overnight. They are then dried in an oven at about 55° C. for about 20 minutes. After drying, those membranes are stored in specific boxes with desiccants under a maximum of 10% of relative humidity. Membranes (referred to as conjugate pad (13)) are cut into about 5 mm width pieces and sticked onto the first adhesive parts of the laminates as indicated in FIGS. 1, 2 and 3. Location of these membranes is important to reach the maximum detectability expected for specific purposes. Absorbent papers made of glass fibers, or any other absorbent matter, are then sticked onto the upper adhesive parts of the strip provided they are in contact either by overlaps, either edge top edge with the polyester membrane containing the conjugates to allow the liquid to rehydrate the conjugates and let them react with the analytes or analogues thereof present in the sample.

When AccuFlow G or Standard 14 or membrane 8964 (Alströhm) membranes are used, the conjugates are sprayed with the IsoFlow Atomizing Nozzle system from Imagen Technology. In this case the conjugates are sprayed at a speed of 50 mm/sec for quantities sprayed ranging from 0.8 µL/mm to 3.0 µL/mm with a pressure ranging from 1 to 20 psi. Membranes are let to dry at room temperature overnight. They are then dried in an oven at about 55° C. for about 10 minutes. After drying, those membranes are stored in specific boxes with desiccants under a maximum of 10% of relative humidity. Membranes (referred to as conjugate pad (13)) are either cut into about 5 to 10 mm width pieces or non cut and sticked onto the upper adhesive parts of the laminates as indicated in FIGS. 1, 2 and 3. Location of these membranes is important to reach the maximum detectability expected for specific purposes. Absorbent papers (Fusion 5 from Whatman) made of glass fibers, or any other absorbent matter, are then sticked onto the upper adhesive parts of the strip provided they are in contact either edge-to-edge or by covering partially or completely the membrane containing the conjugates to allow the liquid to rehydrate the conjugates and let them react with the analytes or analogues thereof present in the sample.

Some tests require that a quantification is performed in order to know whether the concentration of for instance the antigen or whether the serological response to for instance an antigen to be detected is higher or lower than a defined cut-off level. This can be done by comparing the intensity of a test line (specific line (8)) to that of one or several control line(s) (9) of constant or progressive intensities. The reference scale that is obtained as such consists of several lines of different intensities between them, but constant and reproducible for each of them. Each conjugate is hereby preferably dried at a predefined concentration to obtain a constant intensity. The intensity of the test line signal will be proportional to the concentration of for instance the antigen, at least in a desired predefine range of concentrations including the cut-off level.

The present invention also encompasses kits incorporating the device according to the invention, packaging incorporating said device, unitized housings, holders and means for supporting said device. Said support means, also referred to a support member, refer to a material which can act to maintain the gravity driven test device according to the invention in a substantially upright position, with the sample application zone located at the top end of said device. Materials for use as support means include, but are not limited to, glass, plastic and the like.

In another aspect of the present invention, there is provided test kits for detection of at least one analyte or analogue thereof in a sample. These test kits can include, separately packaged, or packaged altogether: a sheet-like gravity driven test device according to the present invention; and optionally, any additional reagents for treating or extracting the sample.

The term "kit" as used herein refers to any combination of reagents or apparatus that can be used to perform a method of the invention. The kit of the invention can further include any additional reagents, buffers, excipients, containers and/or devices as required described herein or known in the art, to practice a method of the invention. Other kit elements can include containers for packaging one or more device elements, packaging materials, aqueous solutions for use with the device, and the like. The above described devices can be packaged and sold as kits for detection of analytes. Indeed, the above devices, being self-contained and convenient for use, are themselves kits.

A set of instructions for directing a user in the use of the devices or methods according to the invention will also be typically included.

In another aspect, the present invention provides an analyte detection method for the detection of at least one analyte in a sample, comprising the step of contacting an assay device with a sample and allowing the sample to move from the top to the bottom of said device by gravity, and detecting the analyte or analogue thereof. In a particular embodiment of the present invention, the analyte detection method comprises the steps of vertically positioning (i.e. positioning in a substantially upright position) the assay device, applying a sample at the top of the device, allowing the sample to migrate through the device thereby allowing analyte in said sample to react with capture reagent and allowing the development of a detectable signal thereby detecting said analyte.

As used herein the term "assay device" encompasses the gravity driven test device according to the invention as well as test strips, dipsticks, diagnostic strip, flow through devices, lateral flow devices and the like. The test strips, dipstick, flow through and lateral flow sticks are conventional in form; therefore, because those of ordinary skill in the art will be abundantly familiar with the design of such test strips, they will not be described in detail here. However, each test strips, dipstick, flow through and lateral flow device will have a test zone for binding of analyte (to indicate a positive test result for the presence of analyte in the analyte sample) and a control zone for binding of tracer (to indicate correct operation of the assay), preferably in capillary communication with each other.

The present method thereby encompasses the use of such assay devices in a substantially upright position, with the sample application zone on the top end of the device, so that when sample is applied, it migrate from top to bottom of the device. It was surprisingly found that even with sample that usually migrates with difficulty because of clogging and viscosity, the method of the invention allowed faster and easier migration of said sample compared to prior art methods wherein the sample is applied at the bottom of the device and the sample is allowed to migrate by capillary action from the bottom to the top of the device.

In another aspect, the present invention concerns an article of manufacture or packaging, suitable for packaging assay device, comprising optionally a label on or associated with the packaging that indicate the content thereof, and a packaging insert containing instructions. Preferably the assay device is selected from the group comprising the gravity driven test device according to the invention, test strips, dipsticks, diagnostic strip, flow through devices, lateral flow devices and the like. Preferably, the test zones and control zones of each test strip lie in the same location on each test strip so each can be viewed in side-by-side fashion. The packaging according to the invention offers rapid access, unit test device accountability and better physical protection for the test device.

Figure 5A:
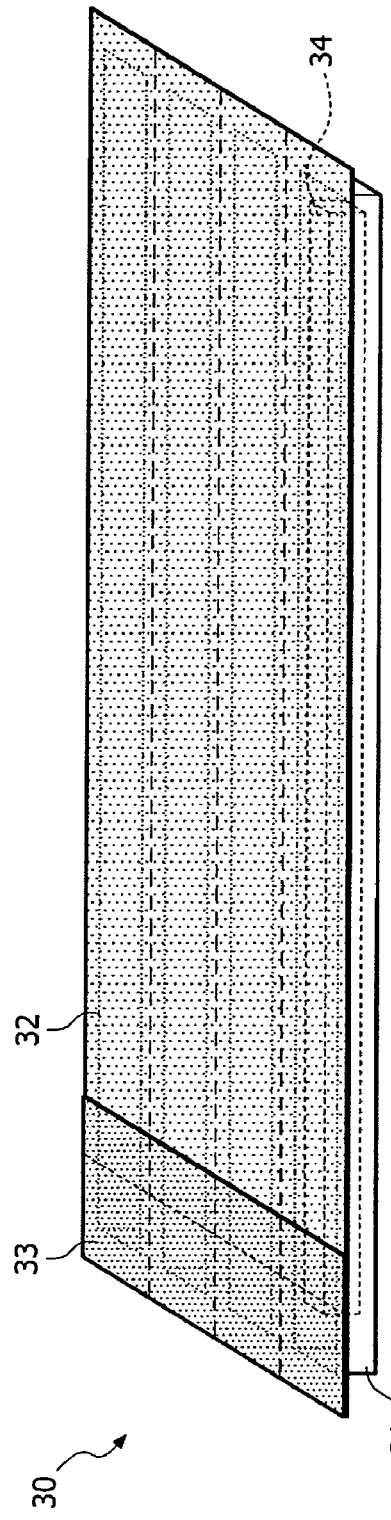
FIG. 5 represents a perspective view (5a) and an exploded view (5b) of a packaging in accordance with embodiments of the present invention.
Figure 5B:
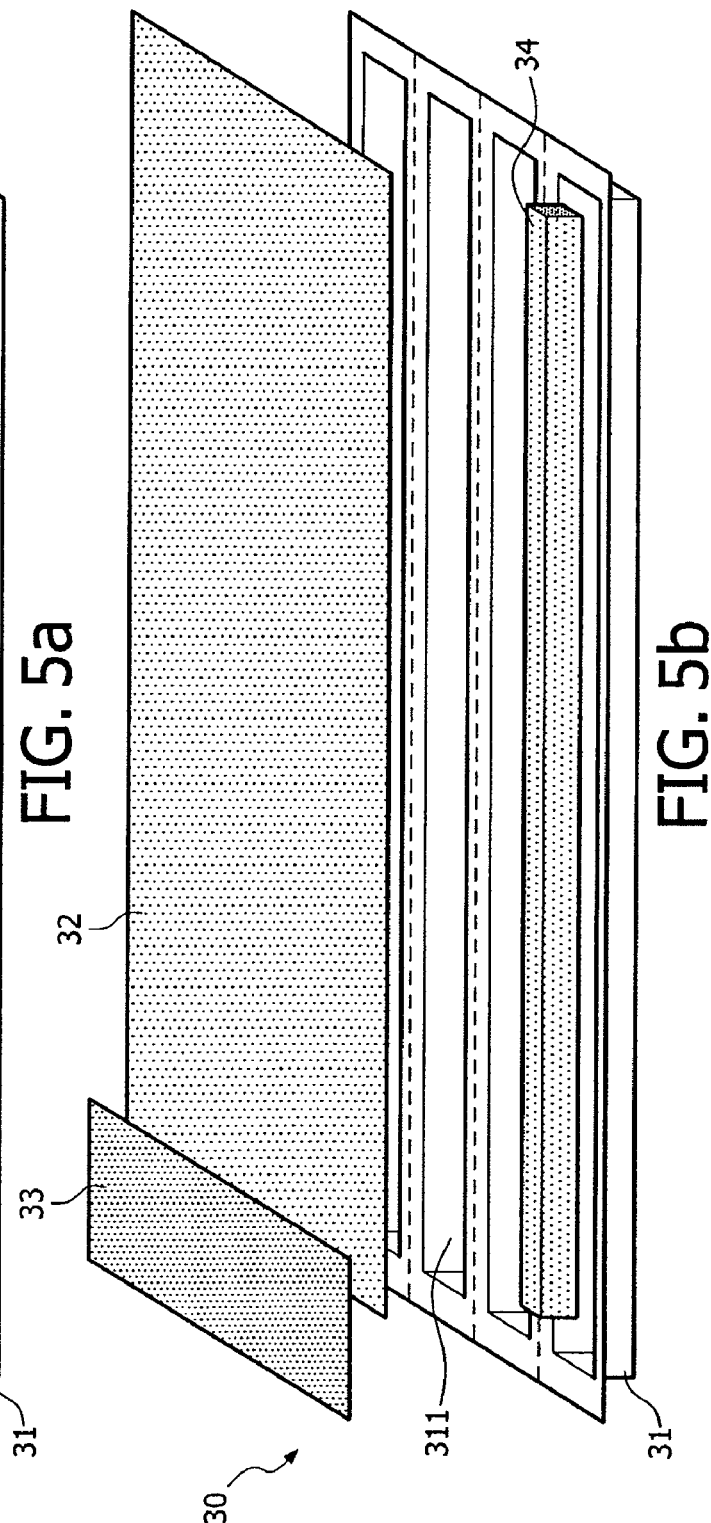
Figures 6A, 6B:
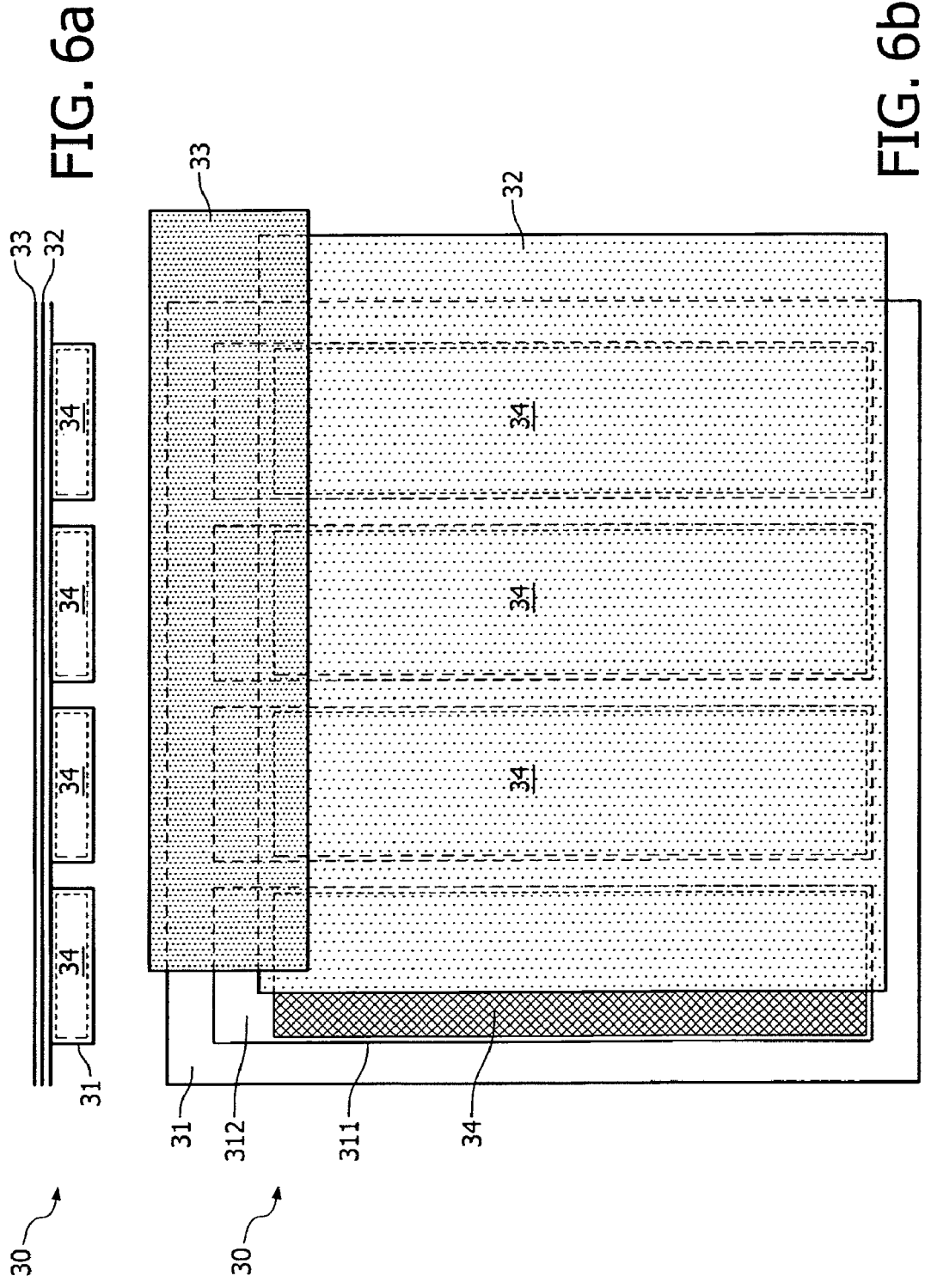
FIG. 6 represents a cross section view (6a) and a semi-exploded front view (6b) of a packaging in accordance with embodiments of the present invention.

FIGS. 5, 6 and 7 illustrate different embodiment of a packaging (30) suitable for Gravity Driven Tests, and/or immuno- and oligochromatography assay devices (34).

Referring to FIG. 5*a*, a packaging (30) according to the invention is comprised of a holder (31) for housing one or more assay devices (34). The holder (31) can be at least partly sealed with a cover sheet (32). Optionally part of the holder (31) is additionally sealed with a removable cover sheet (33) which can be peeled-off, said removable cover (33) is preferably overlapping part of the cover sheet (32). FIG. 5*b* illustrates the packaging according to an embodiment of the invention in an exploded view. A packaging (30) according to the invention is comprised of a holder (31) comprising one or more lodges (311) for housing one or more strips (34). Preferably said lodges (311) are heat formed. Each lodge is separated from the next within the holder (31) by a raised spacer. The lodge (311) is typically rectangular in form, preferably having a width slightly narrower than that of the assay device (34). In an embodiment, the raised spacer can be weakened along its length (for example, can be precut) so as to be able to detach each lodge from each other. Accordingly, the cover sheet and removable cover sheet sealed on the holder can also be provided with corresponding precut lines, for the disconnection of unitized packaging comprising one device.

Said holder (31) is preferably made from a moisture impervious solid material selected from the group consisting of a single metal layer, multiple metal layers, a single plastic layer, multiple plastic layers, and a composite metal and plastic layer, and the cover sheet (32) and/or (33) is a sheet selected from the group consisting of a single metal layer, multiple metal layers, a composite metal and plastic layer, a composite metal and paper layer and a composite metal, plastic and paper layer. Said holder (31) is preferably made from plastic material.

Referring to FIG. 6, the packaging (30) is comprised of a holder (31) comprising one or more lodges (311) for housing one or more assay device (34), wherein one end of said lodges comprise a sample deposit area (312) which can be in direct communication with the end of the assay device (34) having the sample application zone such that a sample can be applied to said assay device (34) through the sample deposit area (312).

The holder is partly sealed with a cover sheet (32) and a removable cover sheet (33) optionally partially overlapping said first cover sheet (32). FIG. 7*b* illustrate a rear view of a packaging (30) according to an embodiment of the invention, wherein the holder (31) is optionally provided with an observation window (35) juxtaposed over at least a portion of the assay device (34) so that at least the detection zone (4) comprised in said assay device (34) is in visual communication with the exterior of the holder (31). Alternatively, the portion of the holder (31) which overlies the detection zones of the assay devices (34) is transparent to permit visually observable results shown in each zone to be viewed. Alternatively, the cover sheet (32) is transparent to permit visually observable results shown in each zone to be viewed.

Assay device (34) may be secured within the lodge (311) by adhesion to the floor of each lodge; however, the placement of cover sheet (32) onto the holder (31) is sufficient to retain the assay devices (34) within the lodge (311). To this end, cover sheet (32) and/or removable cover sheet (33) can be conveniently constructed of an opaque tape having at least one transparent window formed therein for viewing of test results along a sample detection zone. To secure cover sheet (32) onto holder (31), as well as to secure assay device (34), within the lodge (311), cover sheet (32) is pressed into place to form an adhesive attachment between cover (32) and the upper edges of rails of the holder (31). Conveniently, the cover (32) and/or removable cover sheet (33) are also provided with transparent windows through which labels on assay devices (34) can be viewed. The labels (not shown) may be printed with information of use in performing the assay, such as the identity of analyte detectible with each assay device.

The packaging according to the invention are particularly adapted for performing a detection method according to the invention, wherein the assay device after application of a sample on a sample application zone thereof, is vertically positioned such that the sample application zone is at the top end of the device, and wherein the sample is allowed to migrate through the device by gravity. For example, the packaging may be vertically positioned to vertically positioning the assay device. To that end the packaging may comprise additional support means for maintaining in a substantially upright position said packaging.

In use, the packaging (30) comprising one or more assay device (34) is preferably put in an upright position, with the removable cover sheet (33) on the top end of said packaging (30). The removable cover sheet (33) can than be removed to reveal one or more lodges (311) each comprising a sample deposit area (312) and a device (34). Liquid sample containing the analyte or analogue thereof to be detected is settled at the top of the device (34) and migrates through the test zone for binding of analyte and the control zone for binding of tracer and allowing the development of a detectable signal thereby detecting said analyte.

The present invention is further illustrated by the following examples, which are not intended to be limiting in any way.

EXAMPLES

Example 1

Detection of Rotavirus and Enteric Adenovirus 40141 (Group F, Strains 40 & 41)

Preparation of Polystyrene Microspheres:

Polystyrene microspheres (Estapor) are washed in a specific washing buffer (Coris BioConcept). Microspheres are then centrifuged at 13,000 RPM for 5 to 10 minutes for recovering a 1 mL volume. Pellet is then resuspended in the activation buffer and mixed for one hour. Suspension is then washed twice in the washing buffer before to be finally resuspended in the coupling buffer after a final centrifugation.

Coupling of Antibodies to Non-Activated and Amino-Activated Polystyrene Microspheres:

Coupling of the reagent to the polystyrene microspheres was performed essentially following the protocol provided by the manufacturer.

First coupling was performed with a mouse monoclonal antibody directed against Rotavirus group A antigen with blue NH2-polystyrene microspheres.

Second coupling was performed with non-activated red polystyrene microspheres with a mouse monoclonal antibody directed against Enteric Adenoviruses (40 and 41).

Third coupling was performed with non-activated green polystyrene microspheres with naïve chicken IgY.

The immunogravity Driven Test Device:

The sheet-like immunogravity driven test device (1) of the present example consists of a plastic backing solid support (MDI) (2) with thereupon a sample application zone (2) consisting of Fusion 5 (Whatman), covering a conjugate pad (13) consisting of Standard 14 (Whatman) containing the three conjugates, a non capillary zone (14), an intermediate zone (6) consisting of GFBR-1 (MDI), a detection zone (4) made of nitrocellulose (MDI) and an adsorption region (5) made of cellulose (MDI).

The nitrocellulose membrane is sensitized with three reagents. The first reagent encountered is a monoclonal antibody directed against Adenovirus and is localized at the upper part of the active membrane (16) of the detection zone (4). This is defined as the "Ad40/41 test line". The second reagent encountered by the sample is a guinea pig polyclonal antibody directed against Rotavirus and is deposited at the middle part of the active membrane in the sample detection zone. This is defined as the "Rota test line". The third reagent is an anti-chicken IgY polyclonal and it is laid down at the lower part of the active membrane (16) of the detection zone (4). This is defined as the migration control line. Three conjugates are used: the monoclonal antibody directed against rotavirus conjugated to blue NH2-polystyrene microspheres, the monoclonal antibody directed against the enteric adenoviruses (40 and 41) conjugated to the red polystyrene microspheres and the chicken IgY polyclonal conjugated to green polystyrene microspheres. The mix of these three conjugates is deposited in the first reactive zone (3) (Standard 14 from Whatman) of the sample application zone of the device. This membrane is fully covered by the first absorbent membrane (12) (Fusion 5 from Whatman).

The intermediate zone consists of GFBR-1 (MDI) membrane that overlaps by 1 mm the active membrane (16).

A sticker may cover all the three first zones, i.e. the sample application zone, the non capillary zone leading to a space wherein the liquid will move freely by gravity and the intermediate zone. It comes to stick by 2 mm on the active zone (16).

Carrying Out of the Test:

The test with the immunogravity driven test device of the invention is carried out vertically by putting the device in a test tube, the sample application zone being at the top.

Samples containing either Rotavirus or Enteric Adenoviruses (40 or 41) are diluted in a sample buffer. Between 100 to 250 μL of this solution is pipetted and deposited at the top of the device on the sample application zone.

The presence of enteric adenoviruses (40 or 41) will be detected by the appearance of a red line in the upper region of sample detection zone (Ad 40/41 test line), and the presence of Rotavirus will be detected by the appearance of a blue line in the middle region of the detection zone (Rota test line). The migration of the chicken green polystyrene conjugate will react with the coated anti-chicken IgY giving rise to a green migration control line. The test is performed in 10 minutes.

In all cases, the migration control line appears, showing that the sample has migrated from the top to the bottom of the immunogravity driven test device (1).

Example 2

Detection of *Legionella pneumophila* Urinary Antigen

Preparation of Colloidal Gold Particles:

Colloidal gold particles of about 40 nm were purchased from a commercial source (Diagam).

Coupling of Antibodies to Colloidal Gold Particles:

Coupling antibodies to colloidal gold particles is well known in the art. In this example, purified rabbit antibodies directed against *Legionella pneumophila* urinary antigen were used. Purified polyserum was reacted with a colloidal gold particles suspension that had been buffered with a potassium carbonate solution to obtain the desired pH. This pH is predetermined and may be different for each immunological reagent. The dilution of the purified polyserum to be used in the coupling process was defined in a preliminary experiment.

In this preliminary experiment, increasing dilutions of the polyserum were reacted for three minutes with the buffered colloidal gold particles and then sodium chloride was added to reach about 1% final concentration. Absorbance at 630 nm was recorded. The highest dilution of the polyserum at which the absorbance was equal or similar to the absorbance obtained with the lower dilution of the polyserum was chosen as the reference dilution for the coupling of the reagent to the colloidal gold particles.

For the coupling in itself, the polyserum at the chosen dilution and the buffered colloidal gold particles were reacted for three minutes. This so-called conjugate was subsequently saturated and washed several times by centrifugation and resuspension in a washing buffer to remove any unconjugated antibodies and finally resuspended in a conservation buffer.

A second conjugate made of purified chicken IgY polyclonal was used as control conjugate and coupled according to the same protocol as described here above.

The Immunogravity Driven Test Device:

The sheet-like immunogravity driven test device (1) of the present example consists of a plastic backing solid support (MDI) (18) with thereupon an application, a non capillary, an intermediate, a detection and an absorption zones.

The sample application zone (2) consists of AccuflowG (Whatman-Schleicher & Schuell), the intermediate zone (6) consists of GFBR-1 (MDI), the detection region (4) is made of nitrocellulose (MDI) that has preferably, but not limited to, a 10 μm porosity and the absorption region (5) is made of cellulose (MDI).

The nitrocellulose membrane is sensitized with two reagents. The first reagent is a purified rabbit polyserum reagent directed against *Legionella pneumophila* urinary antigen and is deposited in the upper part of the active membrane (16) in the detection zone (4). This is defined as the "Lp test line". The second reagent is a purified rabbit polyserum anti-chicken IgY and will react with the chicken IgY polyclonal coupled to colloidal gold particles. It is deposited in the lower region of active membrane (16) of the detection zone (4). This is defined as the "migration control line". Both specific *Legionella pneumophila* urinary antigen conjugate and chicken IgY control conjugate are impregnated in the AccuflowG (Whatman-Schleicher & Schuell), in the sample application zone (2). In a preferred embodiment, the dilution buffer is sprayed onto the top of the AccuFlow G membrane, giving rise to a test for which no liquid buffer is required.

Carrying out of the Test:

The present test aimed at the detection of *Legionella pneumophila* urinary antigen with the immunogravity driven test device (1) of the invention. It is carried out similarly as described in the first example.

Urine samples containing *L. pneumophila* antigens are diluted in a specific buffer in the ratio of 3V/V. The immunogravity driven test device (1) of the invention is put in a test tube, the sample application zone being at the top. When the specific dilution buffer is already impregnated onto the Accu-Flow G sample membrane, the urine sample is directly put into the application zone.

Between 100 to 250 μL of this solution is pipetted and deposited at the top of the device on the sample application zone.

The test was shown to be specific: The "Lp test line"—appears with a sample containing *L. pneumophila* urinary antigens, and the intensity decreases with increasing dilutions of the sample.

Similarly, the "control line" appears in all cases, with the same intensity even when sample was negative for the urinary antigen. The test is performed in 15 minutes.

What is claimed is:

1. Analyte detection method for the detection of at least one analyte in a sample, comprising the steps of (i) vertically positioning a test device, wherein said test device comprises on one or more sides of the solid support arranged from one end to the other end of the device:

(a) a first capillary zone comprising a sample application zone, (b) a second capillary zone comprising an intermediate zone and a detection zone, disposed next to said intermediate zone, and optionally an absorbent zone or region disposed next to said detection zone, said detection zone optionally comprising a control subzone, (c) a non-capillary zone; separating the sample application zone of the first capillary zone from the intermediate zone of said second capillary zone, wherein said non-capillary zone is configured such as to prevent any direct and capillary contact between the sample application zone and the intermediate zone, and said non-capillary zone provides for a mixing zone;

wherein said sample application zone, said non-capillary zone and said intermediate zone are disposed in a manner such that when the device is in use, sample can flow only by gravity through the non-capillary zone, from the first capillary zone comprising the sample application zone to the second capillary zone comprising the intermediate zone and detection zone, (ii) contacting the sample application zone on the top end of the device with a sample and (iii) allowing the sample to move from said first capillary zone comprising the sample application zone to said second capillary zone comprising the intermediate zone, by gravity through said non-capillary zone, and (iv) detecting the analyte, and wherein steps (i) to (iv) are performed with the device held in a substantially upright position.

2. The analyte detection method according to claim 1, comprising the steps of vertically positioning the test device, applying a sample at the top of the device, allowing the sample to migrate through the sample application zone and hydrate at least one analyte-specific conjugate, allowing an at least one analyte in said sample to react with the at least one analyte-specific conjugate, thereby forming at least one complex, allowing the at least one complex to reach the non-capillary zone, to pass by gravity the non-capillary zone to come in contact and migrate through the intermediate zone and to go through the detection zone thereby reacting with at least one capture reagent specifically recognizing at least one analyte and developing a detectable signal thereby detecting said at least one analyte.

3. The analyte detection method according to claim 1, for the detection of analytes from microorganisms selected from *Cryptosporidium parvum, Toxoplasma gondii, Giardia lamblia, E. coli, E. histolytica, C. difficile, C. difficile* toxins, RSV (Respiratory Syncytial Virus), Influenza-A and -B viruses, Rotavirus, Adenoviruses types 40 & 41, *Legionella pneumophila* urinary antigen, Coronaviruses of human and animal origin and Human Metapneumoviruses.

4. The analyte detection method according to claim 2, wherein said capture reagents specifically recognizing at least one analyte are selected from the group consisting of oligonucleotides or analogues thereof, polyclonal or monoclonal antibodies, hypervariable antibody fragments, an antigen recognized by serological compounds selected from IgG, IgA, IgE and IgM, and biotin-streptavidin.

5. The analyte detection method according to claim 1, wherein the sample application zone further comprises at least one control conjugate.

6. The analyte detection method according to claim 1, wherein the detection zone comprises at least one control test line with at least one control capture reagent specifically recognizing the control conjugate in the application zone.

7. The analyte detection method according to claim 2, wherein the analyte-specific conjugate and/or a control conjugate comprise a label selected from the group consisting of conjugated metallic colloids, conjugated polystyrene microspheres, carbon nanotubes and micro- or nanoparticles with a color, and fluorescent micro- or nanoparticles.

8. The analyte detection method according to claim 1, wherein the detection zone comprises an active membrane made of nitrocellulose or another matrix capable of being coated by capture reagents specifically recognizing at least one analyte.

9. The analyte detection method according to claim 1, wherein the intermediate zone comprises an absorbent membrane.

10. The analyte detection method according to claim 1, wherein a sticker covers the sample application zone, the non-capillary zone, the intermediate zone and overlaps partially the detection zone.

11. The analyte detection method according to claim 1, wherein said device is provided in a hollow casing or a heat-molded casing or is embedded in a polymer.

* * * * *

UNITED STATES PATENT AND TRADEMARK OFFICE
CERTIFICATE OF CORRECTION

PATENT NO. : 8,389,209 B2  
APPLICATION NO. : 12/096008  
DATED : March 5, 2013  
INVENTOR(S) : Mertens et al.

Page 1 of 1

It is certified that error appears in the above-identified patent and that said Letters Patent is hereby corrected as shown below:

In the Specification

In column 15 at line 31, Change "lambila" to --lamblia--.

In column 15 at line 40, Change "11," to --II,--.

In column 16 at line 53, Change "Juxtaposed)" to --(juxtaposed)--.

In column 19 at line 25, Change "Alströhm" to --Ahlstrom--.

In column 22 at line 31, Change "than" to --then--.

In column 24 at line 37, Change "AccuflowG" to --Accuflow G--.

In column 24 at line 55, Change "AccuflowG" to --Accuflow G--.

Signed and Sealed this  
Fifteenth Day of October, 2013

Teresa Stanek Rea  
*Deputy Director of the United States Patent and Trademark Office*